United States Patent
Christopher et al.

(10) Patent No.: US 12,083,504 B2
(45) Date of Patent: Sep. 10, 2024

(54) CATALYSTS AND METHODS FOR GAS PHASE CARBONYLATION

(71) Applicant: The Regents of The University Of California, Oakland, CA (US)

(72) Inventors: Phillip Christopher, Santa Barbara, CA (US); Ji Qi, Santa Barbara, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 17/776,933

(22) PCT Filed: Nov. 16, 2020

(86) PCT No.: PCT/US2020/060725
§ 371 (c)(1),
(2) Date: May 13, 2022

(87) PCT Pub. No.: WO2021/118761
PCT Pub. Date: Jun. 17, 2021

(65) Prior Publication Data
US 2023/0001385 A1 Jan. 5, 2023

Related U.S. Application Data

(60) Provisional application No. 62/935,182, filed on Nov. 14, 2019.

(51) Int. Cl.
*B01J 23/36* (2006.01)
*B01J 23/00* (2006.01)
(Continued)

(52) U.S. Cl.
CPC ............ *B01J 23/36* (2013.01); *B01J 23/002* (2013.01); *B01J 23/40* (2013.01); *B01J 35/617* (2024.01);
(Continued)

(58) Field of Classification Search
CPC ............ B01J 23/36; C07C 51/12; C07C 51/56
See application file for complete search history.

(56) References Cited

U.S. PATENT DOCUMENTS

| 2,729,651 A | 1/1956 | Reppe |
| 2003/0065217 A1* | 4/2003 | Zoeller ................. C07C 51/12 560/232 |

(Continued)

FOREIGN PATENT DOCUMENTS

| JP | 2001224970 | 8/2001 |
| JP | 2001224970 A * | 8/2001 |
| WO | 2014135661 | 9/2014 |

OTHER PUBLICATIONS

Wang, et al., Mesoporous nickel catalyst supported on multi-walled carbon nanotubes for carbon dioxide methanation, International Journal of Hydrogen Energy, 41:967-975(2016). (Year: 2016).*

(Continued)

*Primary Examiner* — Deborah D Carr
(74) *Attorney, Agent, or Firm* — PABST PATENT GROUP LLP

(57) ABSTRACT

Catalysts containing a support and a metal oxide, and reactors and methods of using the catalysts in a carbonylation reaction, such as alcohol carbonylation and ester carbonylation, are described herein. The support is typically chemically inert and has a high surface area. The metal oxide typically contains a transition metal or a mixture of metals, such as rhenium, aluminum, tungsten, molybdenum, or a combination thereof. Typically, the metal oxide is mainly atomically dispersed on the surface of the support, as indicated by STEM. For example, at least 10% of the metal oxide is atomically dispersed on the surface of the support. The method includes (i) exposing a mixture of one or more alcohols or one or more esters and carbon monoxide to the (Continued)

catalyst. Typically, the one or more alcohols or one or more esters and carbon monoxide are in a gas phase.

20 Claims, 12 Drawing Sheets

(51) Int. Cl.
  *B01J 23/40* (2006.01)
  *B01J 35/61* (2024.01)
  *B01J 35/64* (2024.01)
  *C07C 51/12* (2006.01)
(52) U.S. Cl.
  CPC .............. *B01J 35/643* (2024.01); *C07C 51/12* (2013.01); *B01J 2523/74* (2013.01); *C07C 2523/36* (2013.01)

(56) References Cited

U.S. PATENT DOCUMENTS

2015/0225321 A1* 8/2015 Su .......................... B01J 29/40
                                                                   568/861
2016/0199814 A1    7/2016 Bai

OTHER PUBLICATIONS

Translation of JP2001/224970.*
FUJISilysiaChemical'CARiACT',Jul. 4, 2017, retrievedfromweb/20180813003022/https://www.fujisilysia.com/products/cariacU> retrievedMay 3, 2021. (Year: 2021).*
"Plug Flow Reactor", Vapourtec, Jun. 3, 2019, retrieved from <http://web.archive.org/web/20190603084348/https://www.vapourtec.com/flow-chemistry/plugflow-reactor/> retrieved May 4, 2021.
Akarmazyan, et al., "Methanol dehydration to dimethylether over Al2O3 catalysts", Appl. Catal. B Environ., 145:136-148 (2014).
Bare, et al., "Experimental (XAS, STEM, TPR, and XPS) and Theoretical (DFT) Characterization of Supported Rhenium Catalysts", J. Phys. Chem. C, 115(13):5740-5755 (2011).
Barton, et al., "Structure and Electronic Properties of Solid Acids Based on Tungsten Oxide Nanostructures", J. Phys. Chem. B, 103(4):630-640 (1999).
Bhan, et al., "Specificity of Sites within Eight-Membered Ring Zeolite Channels for Carbonylation of Methyls to Acetyls", J. Am. Chem. Soc., 129(16):4919-4924 (2007).
Blasco, et al., "Carbonylation of methanol on metal-acid zeolites: evidence for a mechanism involving a multisite active center", Angew. Chemie—Int. Ed., 46(21):3938-3941 (2007).
Boronat, et al., "Mechanistic differences between methanol and dimethyl ethercarbonylation in side pockets and large channels of mordenite", Phys. Chem. Chem. Phys., 13(7):2603-2612 (2011).
Burcham, et al., "Quantification of Active Sites for the Determination of Methanol Oxidation Turn-over Frequencies Using Methanol Chemisorption and in Situ Infrared Techniques. 1. Supported Metal Oxide Catalysts", Langmuir, 17(20):6164-6174 (2001).
Chauvin, et al., "Chemical counting and characterization of the active sites in the rhenium oxide/alumina metathesis catalyst", J. Chem. Soc., Chem. Commun., 6:462-464 (1992).
Cheung, et al., "Selective carbonylation of dimethyl ether to methyl acetate catalyzed by acidic zeolites", Angew. Chemie Int. Ed., 45(10):1617-1620 (2006).
Cheung, et al., "Site requirements and elementary steps in dimethyl ether carbonylation catalyzed by acidic zeolites", J. Catal., 245(1):110-123 (2007).
Christiansen, et al., "Density Functional Theory-Computed Mechanisms of Ethylene and Diethyl Ether Formation from Ethanol on γ-Al2O3(100)", ACS Catal., 3(9):1965-1975 (2013).
Christiansen, et al., "DFT-driven Multi-Site Microkinetic Modeling of Ethanol Conversion to Ethylene and Diethyl Ether on γ-Al2O3(111)", J. Catal., 323:121-131 (2015).

Clarke, et al., "Infrared Studies of the Mechanism of Methanol Decomposition on Cu/SiO2", J. Catal., 150(1):81-93 (1994).
Conifer, et al., "Lewis Acids and Lewis Acid-Functionalized Ligands in Rhodium-Catalyzed Methyl Acetate Carbonylation", Organometallics, 30(15):4060-4066 (2011).
Corma, et al., "Enzyme-like specificity in zeolites: a unique site position in mordenite for selective carbonylation of methanol and dimethyl ether with CO", J. Am. Chem. Soc., 130(48):16316-16323 (2008).
Dewilde, et al., "Kinetics and Mechanism of Ethanol Dehydration on γ-Al2O3: The Critical Role of Dimer Inhibition", ACS Catal., 3(4):798-807 (2013).
Fielicke, et al., "PDF hosted at the Radboud Repository of the Radboud University Nijmegen", J. Phys. Chem. B, 108(38):14591-14598 (2004).
FUJI Silysia Chemical 'CARiACT', Jul. 4, 2017, retrieved from <http://web.archive.org/web/20180813003022/https://www.fujisilysia.com/products/cariacU> retrieved May 3, 2021.
Fujimoto, et al., "Vapor Phase Carbonylation of Methanol With Solid Acid Catalysts", Chem. Lett., 13:2047 (1984).
Gong, et al., "Nickel-catalyzed carbonylation of methyl acetate to acetic anhydride", J. Mol. Catal. A Chem., 147(1-2):113-124 (1999).
Haynes, "Acetic Acid Synthesis by Catalytic Carbonylation of Methanol", Top. Organomet. Chem., 18:179-205 (2006).
Haynes, "Chapter 1—Catalytic Methanol Carbonylation", Advances in Catalysis, Elsevier, 53(1):1-45 (2010).
Haynes, et al., "Promotion of iridium-catalyzed methanol carbonylation: mechanistic studies of the cativa process", J. Am. Chem. Soc., 126(9):2847-2861 (2004).
Hjortkjaer, et al., "Methanol carbonylation in a liquid flow system catalyzed by a polymer-bound rhodium(I) complex", Appl. Catal., 67(1):269-278 (1990).
Hoffman, et al., "Beating Heterogeneity of Single-Site Catalysts: MgO-Supported Iridium Complexes", ACS Catal., 8(4):3489-3498 (2018a).
Hoffman, et al., "In-situ Observation of Phase Changes of a Silica Supported Cobalt Catalyst for the Fischer-Tropsch Process by the Development of a Synchrotron-Compatible In-situ/Operando Powder X-ray Diffraction Cell", J. Synchrotron Radiat., 25(6):1673-1682 (2018b).
Howard, et al., "C1 to acetyls: catalysis and process", Catal. Today, 18(4):325-354 (1993).
International Search Report for PCT application PCT/US2020/060725 dated May 20, 2021.
Jacob, et al., "1,3-Transposition of Allylic Alcohols Catalyzed by Methyltrioxorhenium", Organometallics, 17(9):1835-1840 (1998).
Jehng, et al., "The dynamic states of silica-supported metal oxide catalysts during methanol oxidation", Catal. Today, 28:335-350 (1996).
Korstanje, et al., "Mechanistic insights into the rhenium-catalyzed alcohol-to-olefin dehydration reaction", Chem. Eur. J., 19(39):13224-13234 (2013).
Kwak, et al., "Molecular Active Sites in Heterogeneous Ir—La/C-Catalyzed Carbonylation of Methanol to Acetates", J. Phys. Chem. Lett., 5(3):566-572 (2014).
Liu, et al., "Methanol Selective Oxidation to Methyl Formate over ReOx/CeO2 Catalysts", Catal. Lett., 120(3-4):274-280 (2008).
Liu, et al., "Selective Hydrodeoxygenation of Vegetable Oils and Waste Cooking Oils to Green Diesel Using a Silica-Supported Ir—ReOx Bimetallic Catalyst", ChemSusChem, 11(9):1446-1454 (2018).
Luzgin, et al., "Interaction of Olefins with Carbon Monoxide on Zeolite H-ZSM-5. NMR Observation of the Friedel-Crafts Acylation of Alkenes at Ambient Temperature", J. Am. Chem. Soc., 118(44):10890-10891 (1996).
Lwin, et al., "Surface ReOx Sites on Al2O3 and Their Molecular Structure-Reactivity Relationships for Olefin Metathesis", ACS Catal., 5(3):1432-1444 (2015).
Maitlis, et al., "Methanol carbonylation revisited: thirty years on", J. Chem. Soc., Dalton Trans., 11:2187-2196 (1996).
Marr, et al., "The carbonylation of methylacetate to acetic anhydride catalysed by [CpRh(CO)2] in the absence of hydrogen", Inorg. Chem. Commun., 3(11):617-619 (2000).

(56) References Cited

OTHER PUBLICATIONS

Miessner, et al., "The influence of support on the geminal dicarbonyl species RhI(CO)2 on supported rhodium catalysts: an IR spectroscopic study", J. Mol. Catal., 36(3):359-373 (1986).
Mishra, et al., "Single-atom dynamics in scanning transmission electron microscopy", MRS Bull., 42(9):644-652 (2017).
Ni, et al., "A green route for methanol carbonylation", Catal. Sci. Technol., 7(20):4818-4822 (2017).
Paulik, et al., "Novel catalysts for the low-pressure carbonylation of methanol to acetic acid", Chem. Commun., 11:1578 (1968).
Polichnowski, "Transition-metal-catalyzed carbonylation of methyl acetate", Chem. Educ., 63(3):206-209 (1986).
Qi, et al., "Abstract: Atomically dispersed Rh-Lewis acid sites pairs for selective methanol carbonylation to acetic acid", Nov. 14, 2019, retrieved from https://aiche.confex.com/aiche/2019/meetingapp.cgi/Paper/573324 retrieved Dec. 22, 2022.
Qi, et al., "Atomically Dispersed Rh Active Sites on Oxide Supports with Controlled Acidity for Gas-Phase Halide-Free Methanol Carbonylation to Acetic Acid", Ind. Eng. Chem. Res., 58(28):12632-12641 (2019a).
Ravel, et al., "Athena, Artemis, Hephaestus: data analysis for X-ray absorption spectroscopy using IFEFFIT", J. Synchrotron Radiat., 12(4):537-541 (2005).
Rehr, et al., "High-order multiple-scattering calculations of x-ray-absorption fine structure", Phys. Rev. Lett., 69(23):3397-3400 (1992).
Ren, et al., "Acid-promoted Ir—La—S/AC-catalyzed methanol carbonylation on single atomic active sites", Chin. J. Catal., 39(6):1060-1069 (2018).
Ren, et al., "Single-atom Rh based bipyridine framework porous organic polymer: A high active and superb stable catalyst for heterogeneous methanol carbonylation", J. Catal., 369:249-256 (2019).
Resasco, et al., "Uniformity is Key in Defining Structure-Function Relationships for Atomically Dispersed Metal Catalysts: The Case of Pt/CeO2", J. Am. Chem. Soc., 142(1):169-184 (2020).
Rice, et al., "The oxidation state of dispersed Rh on Al2O3", J. Chem. Phys., 74(11):6487-6497 (1981).
Ro, et al., "Synthesis of Heteroatom Rh-ReOx Atomically Dispersed Species on Al2O3 and Their Tunable Catalytic Reactivity in Ethylene Hydroformylation", ACS Catal., 9(12):10899-10912 (2021).
Roy, et al., "Mechanistic Study of Alcohol Dehydration on γ-Al2O3", ACS Catal., 2(9):1846-1853 (2012).
Schrod, et al., "Kinetic investigations of the synthesis of acetic anhydride by homogeneous catalysis", Ind. Eng. Chem. Prod. Res. Dev., 20(4):649-653 (1981).
Secordel, et al., "TiO2-supported rhenium oxide catalysts for methanol oxidation: Effect of support texture on the structure and reactivity evidenced by an operando Raman study", Catal. Today, 155:177-183 (2010).
She, et al., "Highly Dispersed and Active ReOx on Alumina-Modified SBA-15 Silica for 2-Butanol Dehydration", ACS Catal., 2(6):1020-1026 (2012).
Stepanov, et al., "NMR Observation of the Koch Reaction in Zeolite H-ZSM-5 under Mild Conditions", J. Am. Chem. Soc., 117(12):3615-3616 (1995).
Sunley, et al., "High productivity methanol carbonylation catalysis using iridium: The Cativa™ process for the manufacture of acetic acid", Catal. Today, 58(4):293-307 (2000).
Tang, et al., "Targeting IFNα to tumor by anti-PD-L1 creates feedforward antitumor responses to overcome checkpoint blockade resistance", Nat. Commun., 9(1):1-11 (2018).
Tsoncheva, et al., "Effect of rhenium on copper supported on activated carbon catalysts for methanol decomposition", J. Mol. Catal. A Chem., 225:245-251 (2005).
Tsoncheva, et al., "Rhenium and manganese modified activated carbon as catalyst for methanol decomposition", Can. J. Chem., 85(2):118-123 (2007).
Vicente, et al., "Interactions Involving Lewis Acidic Aluminum Sites in Oxide-Supported Perrhenate Catalysts", J. Phys. Chem. C, 115(18):9012-9024 (2011).
Wang, et al., "Mesoporous nickel catalyst supported on multi-walled carbon nanotubes for carbon dioxide methanation", International Journal of Hydrogen Energy, 41:967-975 (2016).
Wikipedia, "Mesoporous Materials", Jul. 12, 2019, retrieved from <https://en.wikipedia.org/w/index.php?title=Mesoporous_material&oldid=905992070> retrieved May 3, 2021.
Wikipedia, "Microporous Materials", Sep. 16, 2019, retrieved from <https://en.wikipedia.org/w/index.php?title=Microporous_material&oldid=916015841 > retrieved May 3, 2021.
Wikipedia, "Pascal (unit)", Dec. 25, 2018, retrieved from <https://en.wikipedia.org/w/index.php?title=Pascal_(unit)&oldid=875328422> retrieved May 3, 2021.
Yashima, et al., "Vapor phase carbonylation of methanol over Rh-Y zeolite", J. Catal., 59(1):53-60 (1979).
Yates, et al., "Infrared spectroscopic investigation of the rhodium gem-dicarbonyl surface species", J. Chem. Phys., 79(2):1026-1030 (1983).
Zhou, et al., "Identification of active Zr—WOx clusters on a ZrO2 support for solid acid catalysts", Nat. Chem., 1(9):722-728 (2009).
Zhou, et al., "Methanol carbonylation over copper-modified mordenite zeolite: A solid-state NMR study", Solid State Nucl. Magn. Reson., 80:1-6 (2016).
Zhu, et al., "Organic Reactions Catalyzed by Methylrhenium Trioxide: Dehydration, Amination, and Disproportionation of Alcohols", J. Org. Chem., 61(1):324-328 (1996).
Kwak, et al., "Heterogeneous Catalysis on Atomically Dispersed Supported Metals: CO2 Reduction on Multifunctional Pd Catalysts", ACS Catal., 3:2094-2100 (2013).

\* cited by examiner

CATALYSTS AND METHODS FOR GAS PHASE CARBONYLATION

CROSS-REFERENCE TO RELATED APPLICATIONS

This application is a National Phase application under 35 U.S.C. § 371 of PCT/US2020/060725, filed Nov. 16, 2020, which claims the benefit of and priority to U.S. Provisional Application No. 62/935,182 filed Nov. 14, 2019, which are hereby incorporated by reference in their entirety.

STATEMENT REGARDING FEDERALLY SPONSORED RESEARCH OR DEVELOPMENT

This invention was developed under federal funding through grant no. FA9550-15-10022 awarded by the Air Force Office of Scientific Research (AFOSR). The Government has certain rights in the invention.

FIELD OF THE INVENTION

The invention is generally in the field of catalysts, particularly catalysts for carbonylation reactions, such as alcohol carbonylation and ester carbonylation.

BACKGROUND OF THE INVENTION

Acetic acid (AA) is one of the most important bulk commodity chemicals with a worldwide production of more than 10 million tonnes per year, and is used as a precursor for the production of vinyl acetate, acetic anhydride, and acetic esters, among others (Haynes, A., *Advances in Catalysis*, Elsevier, 2010; Vol. 53, Chapter 1, 1-45). Monsanto commercialized an Rh-based homogeneous catalyst for the carbonylation of methanol to produce acetic acid, under reaction conditions of 180-220° C. and 2-4 MPa (Paulik, et al., *Chem. Commun.*, 1968, 11, 1578). BP Chemicals developed the Cativa process, which uses an Ru-promoted Ir catalyst and is similar in process operation to the Monsanto process. Although both of these processes require methyl-iodide to participate in each catalytic turnover (Maitlis, P. M.; Haynes, A.; Sunley, G. J.; Howard, M. J., *J. Chem. Soc., Dalton Trans.*, 1996, 11, 2187), and are operated in the liquid phase, the Cativa process is reported to exhibit higher catalytic activity at lower water content and produce less byproducts compared to the Monsanto process (Sunley, et al., *Catal. Today*, 2000, 58, 293). However, current methanol carbonylation processes require the separation of catalysts and water, in addition to the use of halides, which increases process costs and environmental concerns (Haynes, A., *Top. Organomet. Chem.*, 2006, 18, 179; Ni, et al., *Catal. Sci. Technol.*, 2017, 7, 4818).

Current attempts to immobilize organometallic complexes on solid supports require the use of halides and water in the catalytic process, which minimizes the potential benefit of the immobilized catalysts (Howard, et al., *Catal. Today*, 1993, 18, 325; Hjortkjær, et al., *Appl. Catal.*, 1990, 67, 269; U.S. Pat. No. 2,729,651 to Arnold, et al).

There have been reports that halide-free, gas-phase methanol carbonylation to acetic acid can be achieved using zeolites, such as H-mordenite (H-MOR) (Fujimoto, et al., *Chem. Lett.*, 1984, 13, 2047). In these systems, methanol adsorbs on Brønsted acid sites to form methoxy groups, which can react directly with gas phase CO to form an acylium cation that can be quenched by $H_2O$ to produce acetic acid (Stepanov, et al., *J. Am. Chem. Soc.*, 1995, 117, 3615; Luzgin, et al., *J. Am. Chem. Soc.*, 1996, 118, 10890). Further promotion of reactivity can be achieved by using Cu-modified H-MOR (Cu-MOR), where CO adsorbed to Cu cations promotes the rate of CO insertion into methoxy species on nearby acid sites through a bifunctional mechanism (Zhou, et al., *Solid State Nucl. Magn. Reson.*, 2016, 80, 1).

However, methoxy species on acidic sites can also react with gas phase methanol to produce dimethyl ether (DME) and Cu promotes carbonylation of dimethyl ether to produce methyl acetate (Blasco, et al., *Angew. Chem., Int. Ed.*, 2007, 46, 3938). As a result of these alternate reaction pathways, high selectivity to acetic acid requires process operation at high CO to methanol ratios (i.e., >50:1 molar ratio), which would necessitate the use of very large recycle streams in industrial processes (Ni, et al., *Catal. Sci. Technol.*, 2017, 7, 4818).

There remains a need for improved catalysts and methods for carbonylation reactions, such as alcohol carbonylation and/or ester carbonylation, particularly ones that are suitable for industrial scale use.

Therefore, it is an object of the present invention to provide improved catalysts for carbonylation reactions, such as alcohol carbonylation and/or ester carbonylation.

It is also an object of the present invention to provide reactors for use with improved catalysts for carbonylation reactions, such as alcohol carbonylation and/or ester carbonylation.

It is another object of the present invention to provide methods of using catalysts for carbonylation reactions, such as alcohol carbonylation and/or ester carbonylation.

SUMMARY OF THE INVENTION

Catalysts containing a support and a metal oxide are described herein. Methods of catalyzing carbonylation reactions (such as an alcohol carbonylation reaction and/or ester carbonylation reaction) using the catalysts are also described.

The support is typically chemically inert and has a high surface area. The metal oxide typically contains a transition metal or a mixture of metals including a transition metal, such as rhenium, aluminum, tungsten, molybdenum, or a combination thereof. Typically, the metal forming the metal oxide is present in an amount of at least 0.1 wt % of the catalyst. For example, the metal forming the metal oxide is present in an amount between 0.1 wt % and 10 wt % of the catalyst, such as between 1 wt % and 10 wt % of the catalyst.

Typically, the metal oxide is mainly atomically dispersed on the surface of the support, as indicated by scanning transmission electron microscope (STEM). For example, at least 10% of the metal oxide is atomically dispersed on the surface of the support.

The methods of catalyzing carbonylation reactions typically include the step of exposing a mixture of one or more alcohols or one or more esters, and carbon monoxide to the catalyst, in a reactor. Typically, the one or more alcohols or one or more esters, and carbon monoxide are in the gas phase. Optionally, the methods include oxidizing the metal oxide with an oxidizing gas prior to exposing the reactants to the catalyst. Optionally, the methods include recycling a gas stream after the reactants are exposed to the catalyst.

or "Re/SiO$_2$") as a function of Re weight loading, measured by in situ UV-vis spectroscopy. The measured bandgap energies of reference compounds, KReO$_4$ and Re$_2$O$_7$, are included for comparison.

Figure 2A:
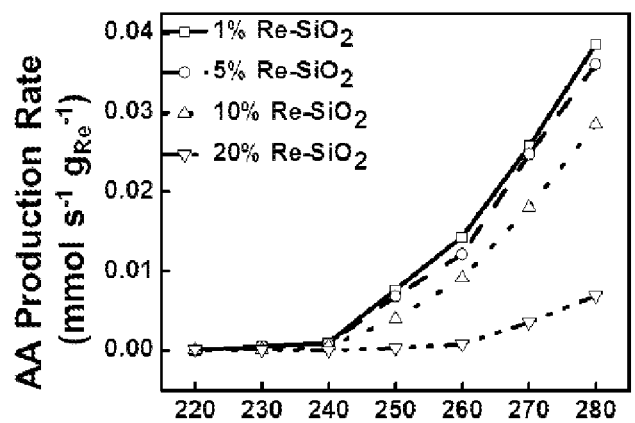
Figure 2B:
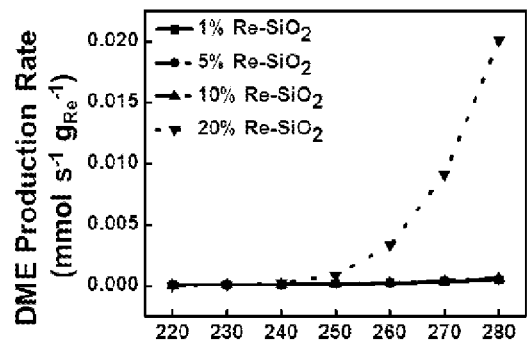

FIGS. 2A-2B are graphs showing acetic acid (AA) production rate (FIG. 2A) and dimethyl ether (DME) production rate (FIG. 2B) on 1%, 5%, 10% and 20% ReO$_x$/SBA-15 catalysts at 33 mbar methanol and 33 mbar CO as a function of temperature. Before catalytic performance measurement, the catalysts were exposed to oxygen gas at 350° C. for 1 h.

Figure 3:
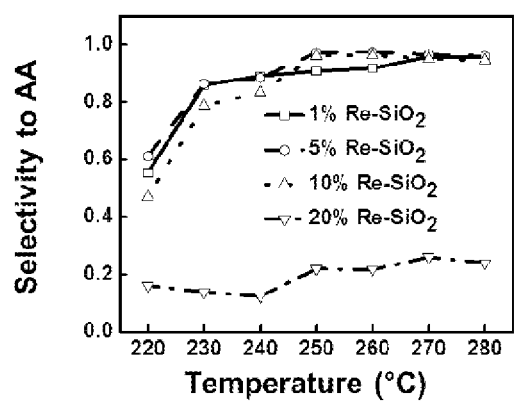

FIG. 3 is a graph showing acetic acid (AA) selectivity on 1%, 5%, 10% and 20% ReO$_x$/SBA-15 catalysts at 33 mbar methanol and 33 mbar CO as a function of temperature. Before catalytic performance measurement, the catalysts were exposed to oxygen gas at 350° C. for 1 h.

Figure 4:
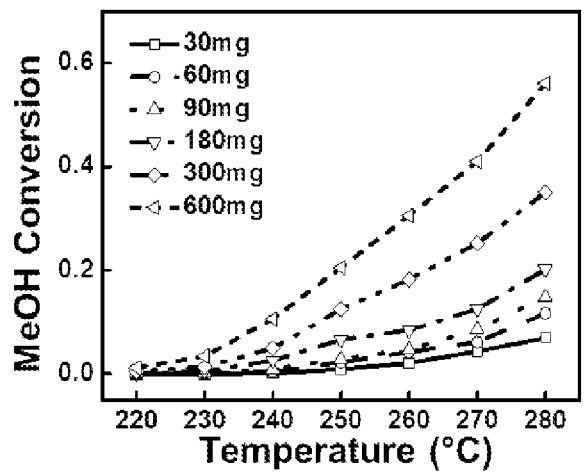

FIG. 4 is a graph showing methanol conversion as a function of different weights of 10% ReO$_x$/SBA-15.

Figure 5:
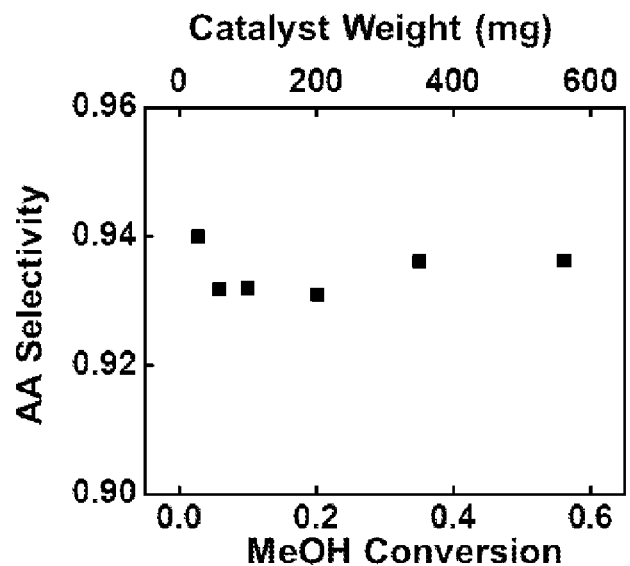

FIG. 5 is a graph showing acetic acid (AA) selectivity as a function of different catalysts weight and methanol conversion (30 mg 10% ReO$_x$/SBA-15 catalyst diluted in 600 mg SiO$_2$ balanced with 270 mg SBA-15; 60 mg 10% ReO$_x$/SBA-15 diluted in 600 mg with 240 mg SBA-15; 90 mg 10% ReO$_x$/SBA-15 diluted in 600 mg SiO$_2$ with 210 mg SBA-15; 180 mg 10% ReO$_x$/SBA-15 diluted in 600 mg SiO$_2$ with 120 mg SBA-15; 300 mg ReO$_x$/SBA-15 diluted in 600 mg SiO$_2$; 600 mg 10% ReO$_x$/SBA-15 diluted in 600 mg SiO$_2$).

Figure 6:
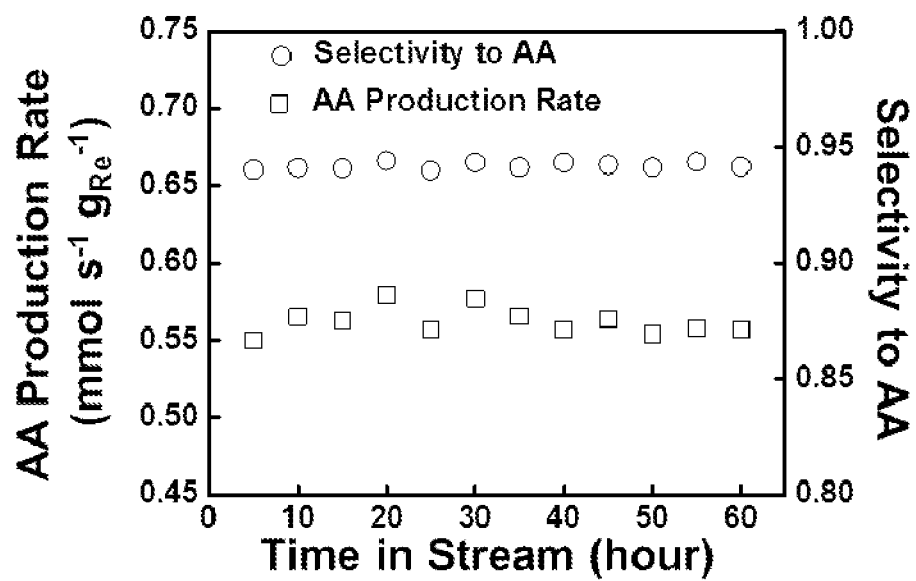

FIG. 6 is a graph showing the stability of 600 mg 10% ReO$_x$/SBA-15 catalysts diluted in 600 mg SiO$_2$ at 280° C., evaluated by methanol conversion and selectivity to acetic acid of the catalyst at different reaction time (i.e., time in stream).

Figure 7:
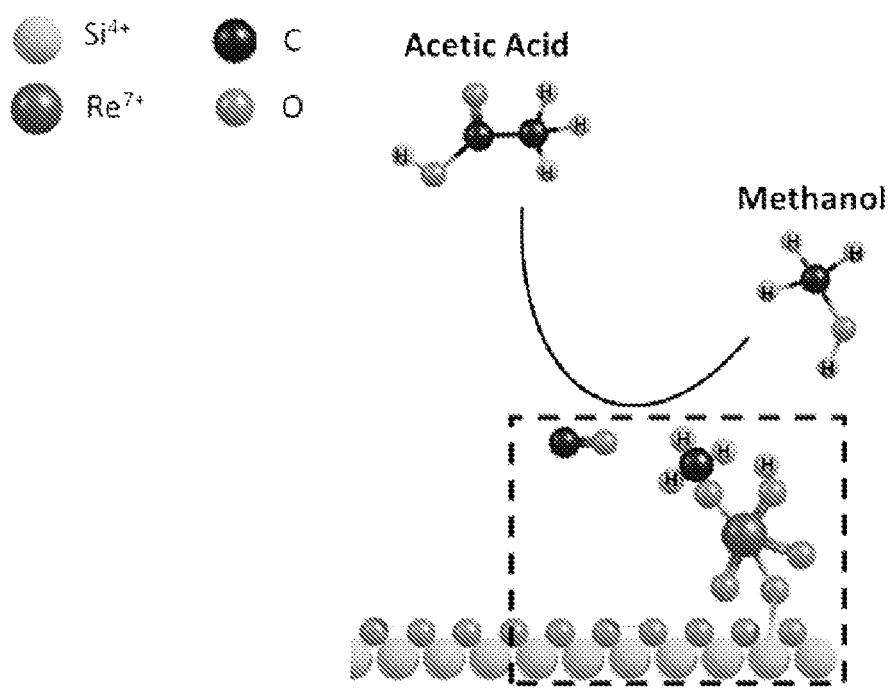

FIG. 7 is a schematic showing an exemplary methanol carbonylation reaction on ReOx/SBA-15 catalysts.

Figure 8:
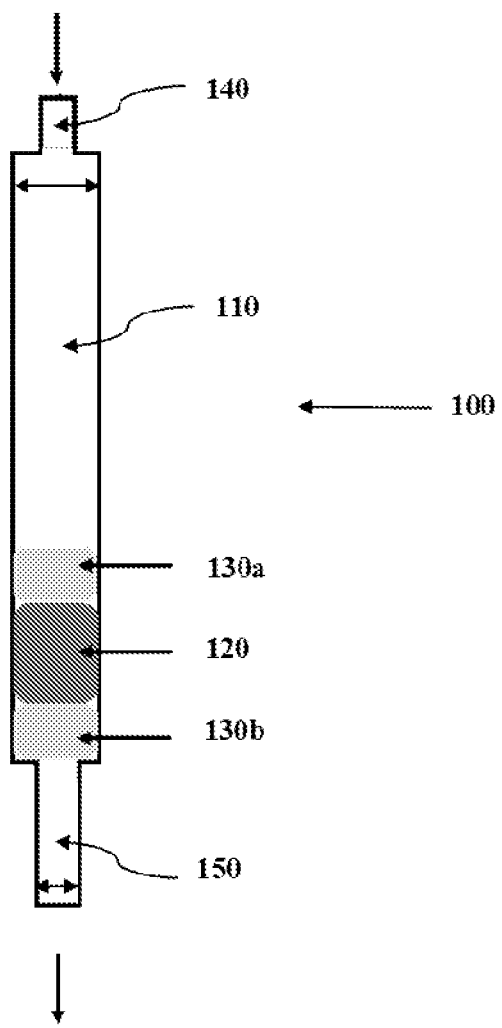

FIG. 8 is a cross sectional view of an exemplary gas phase plug flow reactor containing a bed comprising a catalyst described herein.

Figure 9:
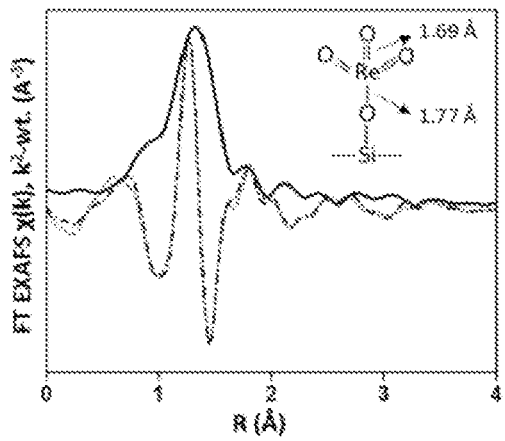

FIG. 9 is a graph showing EXAFS of 5 wt % Re/SiO$_2$ after 1 h oxidation in 20% O$_2$/He at 350° C. The magnitude and imaginary portion of the Fourier transformed EXAFS are represented by the solid and dashed lines, respectively, while the fit to the imaginary portion is shown in dotted line. The inset shows the model used to fit the EXAFS spectrum.

Figure 10A:
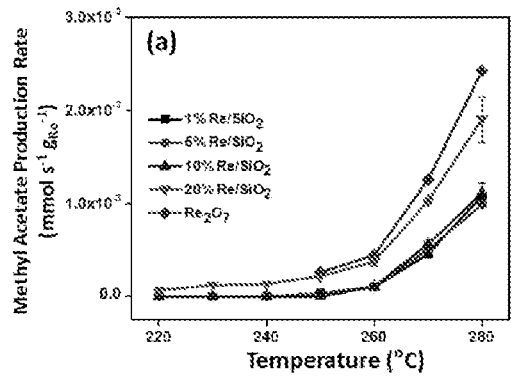
Figure 10B:
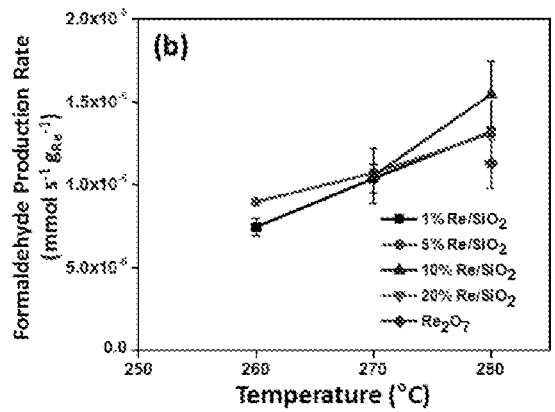

FIGS. 10A-10B are graphs showing production rate of methyl acetate (FIG. 10A) and formaldehyde (FIG. 10B) measured at 30 mbar methanol and 30 mbar CO (balance He) as a function of temperature on 1, 5, 10 and 20 wt. % Re/SiO$_2$. There is no measurable formaldehyde formation at lower temperature.

Figure 11:
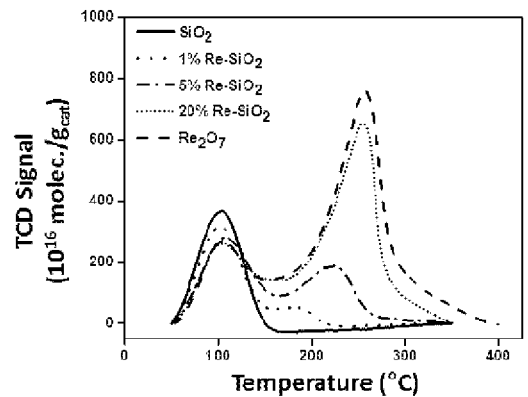

FIG. 11 is a graph showing NH$_3$-TPD signals for SiO$_2$, 1 wt. % Re/SiO$_2$, 5 wt. % Re/SiO$_2$, 20 wt. % Re/SiO$_2$, and bulk Re$_2$O$_7$ (Sigma-Aldrich, 1314-68-7) physically mixed with SiO$_2$ (the amount of Re$_2$O$_7$ and SiO$_2$ were adjusted to provide 20 wt. % Re/SiO$_2$). All catalysts were pretreated in O$_2$ at 350° C. for 1 h. A mixture of 10% NH$_3$/90% He was flown over the catalyst at 50° C. for 1 h. The TPD measurements were carried out in the range 50-350° C. at a heating rate of 10° C./min under He. The peak at 100° C. represents the weak acid sites on SiO$_2$ and the 200-250° C. peak represents the acid sites created by ReOx species.

Figure 12:
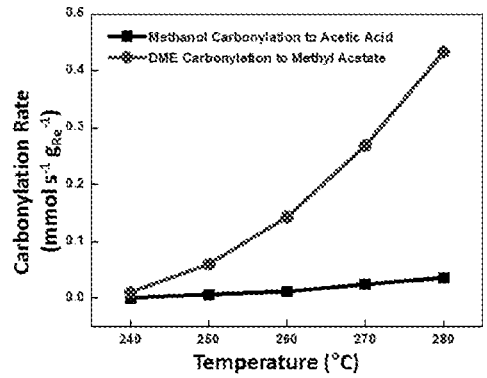

FIG. 12 is a graph showing reaction rate for methanol carbonylation to acetic acid and dimethyl ether carbonylation to methyl acetate on 5 wt % Re/SiO$_2$ from 240 to 280° C. under 30 mbar methanol or dimethyl ether and 30 mbar CO (balance He).

Figure 13A:
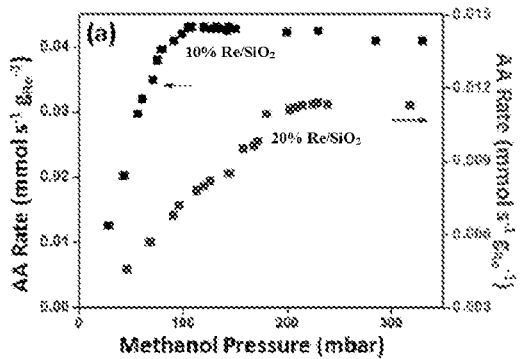
Figure 13B:
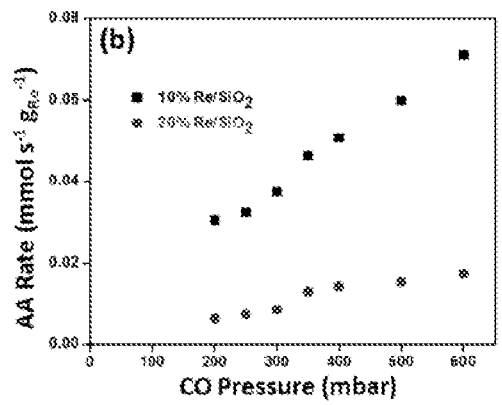

FIGS. 13A-13B are graphs showing acetic acid production rates as a function of methanol partial pressure (FIG. 13A) and CO partial pressure (FIG. 13B) over 10 wt % Re/SiO$_2$ and 20 wt % Re/SiO$_2$. In both sets of experiments, the non-varied reactant partial pressure was held constant at 30 mbar. Before reactivity experiments, the catalyst was oxidized at 350° C. for 1 h.

Figure 14:
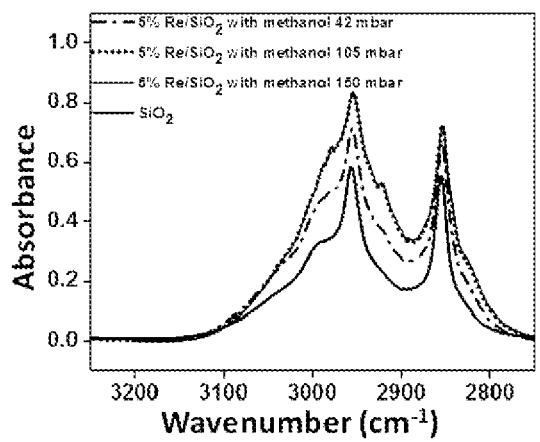

FIG. 14 is a graph showing comparison of in situ FTIR spectra for SiO$_2$ and 5 wt. % Re/SiO$_2$. The 5 wt. % Re/SiO$_2$ sample was oxidized at 350° C. for 1 h before being exposed to 42, 105 and 150 mbar methanol with CO partial pressure the same as 30 mbar (balanced by He). The SiO$_2$ sample was oxidized at 350° C. for 1 h before being exposed to 150 mbar methanol with CO partial pressure as 30 mbar (balanced by He). The spectra were collected under methanol and CO. On SiO$_2$, two strong bands at 2954 and 2854 cm$^{-1}$ correspond to intact methanol on SiO$_2$ and a weak shoulder at 2996 cm$^{-1}$ represents CH$_3$O— on SiO$_2$.

Figure 15:
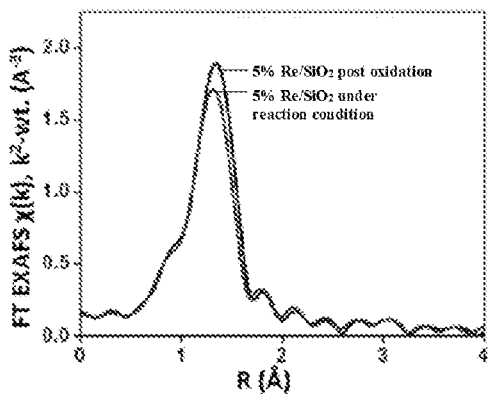

FIG. 15 is a graph showing EXAFS spectra collected at 50° C. after 350° C. oxidation and 250° C. reaction condition for 5 wt % Re/SiO$_2$.

Figure 16:
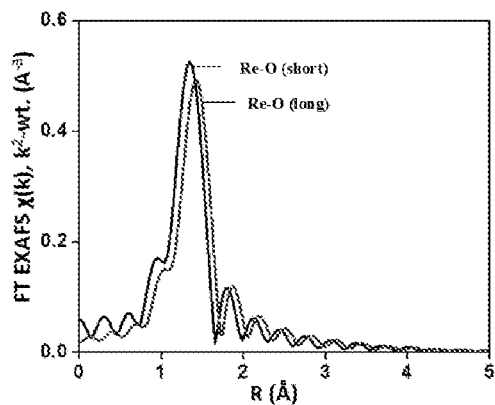

FIG. 16 is a graph showing magnitude of FT of the short and long Re—O scattering paths used in this work. For both paths, $S_o^2=0.73$, N=1, and $\sigma^2=0$ in order to compare the relative magnitude of the two paths. There is a decreased peak intensity for longer Re—O (single) bonds compared to the shorter Re═O (double) bond. The decrease in intensity for the major peak for in-situ vs oxidized data (see FIG. 15) may be consistent with the proposed mechanism in which Re—O single bond coordination increases and Re═O double bond coordination decreases.

Figure 17A:
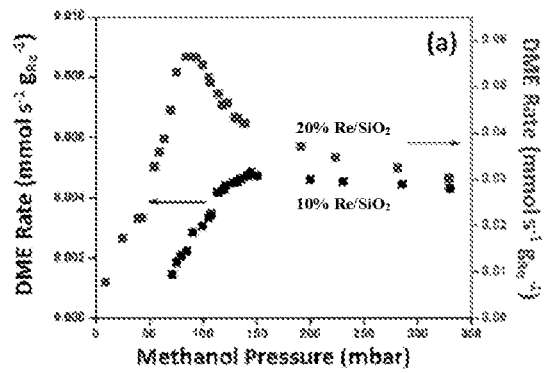
Figure 17B:
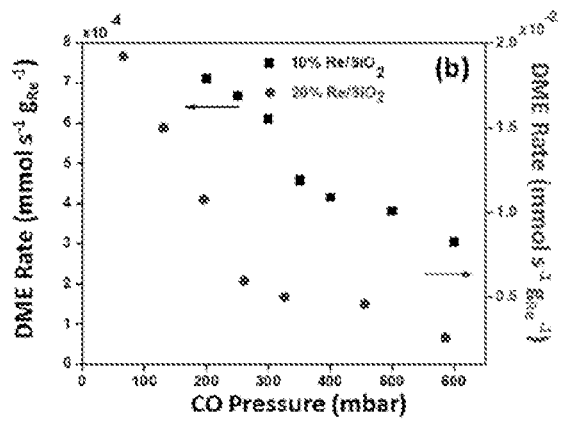

FIGS. 17A-17B are graphs showing DME production rates as a function of methanol partial pressure (FIG. 17A) and CO partial pressure (FIG. 17B) over 10 wt % Re/SiO$_2$ and 20 wt % Re/SiO$_2$. In both sets of experiments, the non-varied reactant partial pressure was held constant at 30 mbar. Before reactivity experiments, the catalyst was oxidized at 350° C. for 1 h.

Figure 18A:
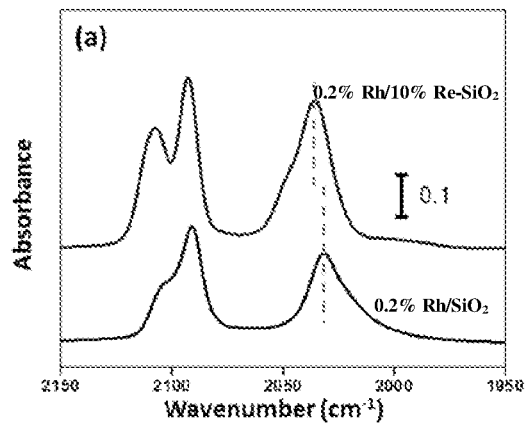
Figure 18B:
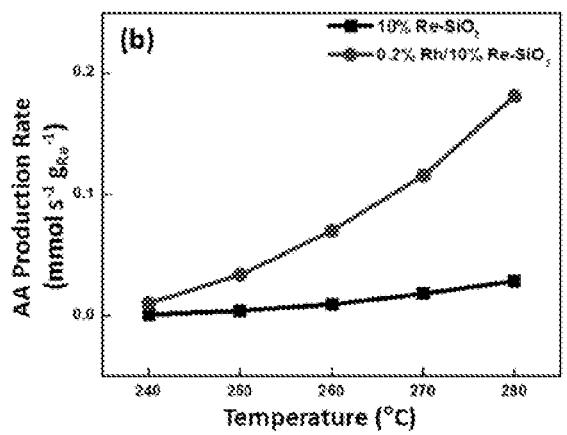

FIG. 18A is a graph showing CO probe molecule FTIR spectra of Rh/SiO$_2$ and Rh/ReOx-SiO$_2$ catalysts. The catalysts were reduced at 250° C. under CO and spectra were collected under Ar. FIG. 18B is a graph showing acetic acid production rate comparison between 10 wt % Re/SiO$_2$ and 0.2 wt Rh/10 wt % Re—SiO$_2$. The catalysts were oxidized at 350° C. for 1 h before being exposed to the reaction condition (30 mbar methanol and CO).

Figure 19:
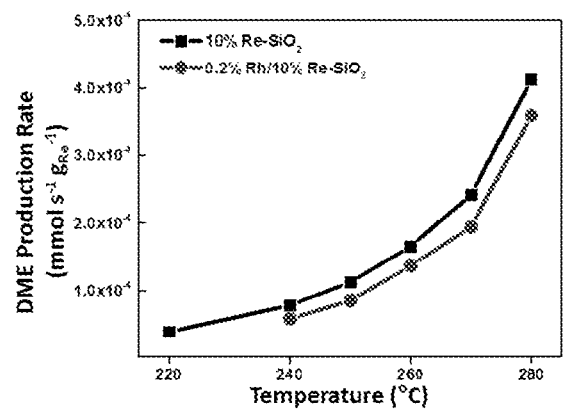

FIG. 19 is a graph showing dimethyl ether formation rate on 10 wt. % Re/SiO$_2$ and 0.2 wt. % Rh/10 wt. % Re—SiO$_2$ during methanol carbonylation from 200 to 280° C. under 30 mbar methanol and CO (balance He).

Figure 20:
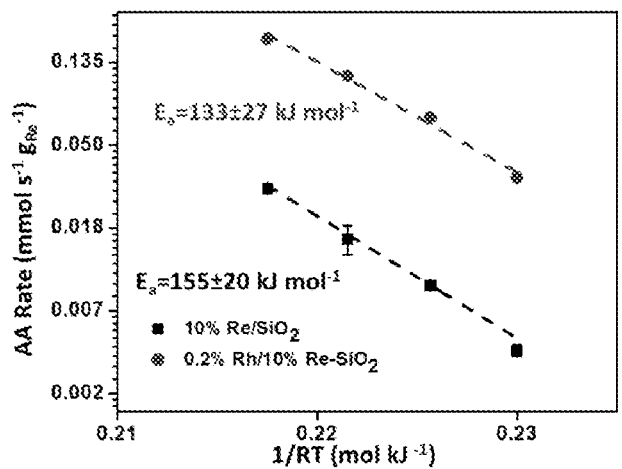

FIG. 20 is a graph showing Arrhenius plots of the acetic acid formation rate on 10 wt. % Re/SiO$_2$ and 0.2 wt. % Rh/10 wt. % Re—SiO$_2$ during methanol carbonylation from 250 to 280° C. under 30 mbar methanol and CO (balance He). The error bars on 10 wt. % Re/SiO$_2$ represent the standard deviation calculated from 2 independently run reactions. The error on Eapp estimates is the 90% confidence interval of the fit.

Figure 21A:
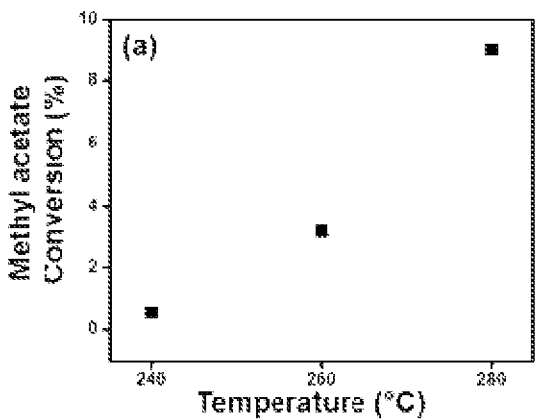
Figure 21B:
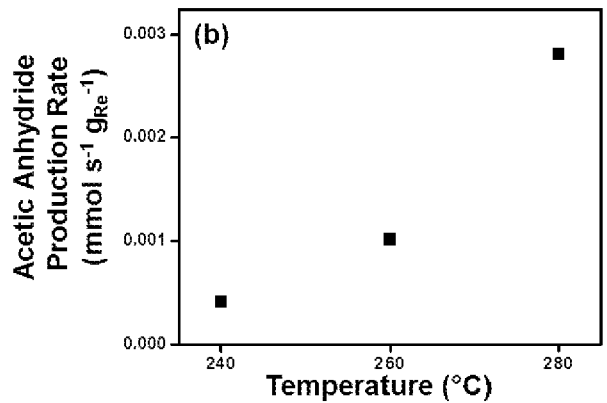
Figure 21C:
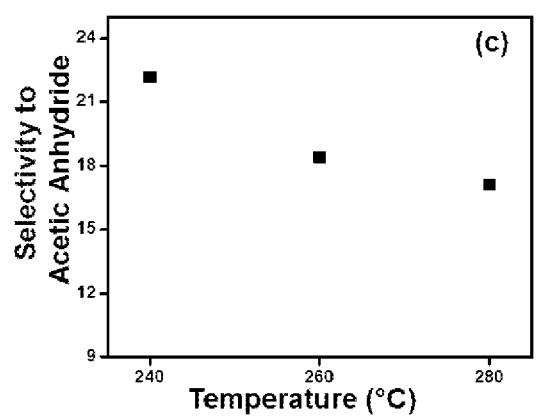

FIGS. 21A-21C are graphs showing methyl acetate conversion (FIG. 21A), acetic anhydride production rate (FIG. 21B), and acetic anhydride selectivity (FIG. 21C) on 10 wt % Re/SiO$_2$ at 177 mbar methyl acetate and 177 mbar CO as a function of temperature. Before catalytic performance measurement, the catalysts were pre-treated at 350° C. for 1 h.

DETAILED DESCRIPTION OF THE INVENTION

I. Catalysts

Catalysts described herein generally include a support and a metal oxide, and are generally suitable for use in heterogeneous reactions, such as catalytic carbonylation reactions, for example, alcohol carbonylation and ester carbonylation. The metal oxide is dispersed on the surface of the support.

A. Support

The support includes suitable support materials, it can be in a variety of suitable forms, and is has a high surface area.

1. Materials for Support

The material for the support is generally chemically inert, i.e. non-acidic and non-basic, and is porous. The material for the support is typically not an acidic material or a material that can become acidic, such as zirconium dioxide. The material for the support is typically not a basic material, such as magnesium oxide. The chemically inert material for the support does not react with any of the reactants and products in the catalytic reaction for which it is selected for use.

a. Chemically Inert Materials

Examples of suitable chemically inert materials for the support include, but are not limited to, silicon dioxide and carbon-based materials.

A carbon-based material generally refers to a material where the number of carbon atoms are at least 50% of the total number of atoms in the material. Examples of suitable carbon-based materials for the support include, but are not limited to, activated carbon, carbon nanotubes, carbon black, and graphene.

b. Porosity

Generally, the material for the support is a mesoporous material or a microporous material. In some embodiments, the material for the support is a mesoporous material and has an average pore diameter from 1 nm to 50 nm. For example, the material for the support is a mesoporous material and the mesoporous material has an average pore diameter of at least 1 nm, at least 2 nm, at least 3 nm, at least 4 nm, up to 50 nm, up to 40 nm, up to 30 nm, up to 10 nm, between 1 nm and 40 nm, between 1 nm and 30 nm, between 1 nm and 20 nm, between 1 nm and 15 nm, between 1 nm and 10 nm, or between 5 nm and 15 nm. For example, the material for the support can be mesoporous silicon dioxide nanoparticles with an average pore diameter between 5 nm and 15 nm, such as SBA-15 (Sigma-Aldrich).

In other embodiments, the material for the support is a microporous material and has an average pore diameter up to 1 nm, such as from 0.4 nm to 1 nm. For example, the material for the support is a microporous material and the microporous material has an average pore diameter of up to 1 nm, up to 0.9 nm, up to 0.8 nm, up to 0.7 nm, at least 0.4 nm, at least 0.5 nm, between 0.4 nm and 1 nm, between 0.5 nm and 1 nm, between 0.4 nm and 0.9 nm, or between 0.4 nm and 0.8 nm. For example, the material for the support is microporous silicon dioxide (e.g. siliceous zeolites) with an average pore diameter between 0.4 nm and 1 nm.

2. Forms of the Support

The support can be in a variety of suitable forms, such as a sheet, powder, particles, microparticles, and/or nanoparticles. For example, the support can be in the form of silicon dioxide nanoparticles or silicon microparticles. In some embodiments, the support can be in the form of a carbon sheet (e.g. graphene sheet), carbon powder, carbon particles, or carbon nanoparticles (e.g. carbon nanotubes).

When the support is in the form of microparticles, the microparticles can have an average diameter up to 500 μm, up to 400 μm, up to 300 μm, up to 200 μm, up to 150 μm, up to 100 μm, up to 10 μm, or up to 5 μm. For example, the support can be silicon dioxide nanoparticles having an average diameter less than 150 μm.

When the support is in the form of nanoparticles, the nanoparticles can have an average diameter up to 1 μm, up to 500 nm, up to 200 nm, up to 100 nm, up to 50 nm, up to 20 nm, up to 10 nm, or up to 5 nm.

When the support is in the form of a carbon sheet, such as a graphene sheet, the sheet can have a dimension on the order of 900 μm, 800 μm, 700 μm, 600 μm, 500 μm, 400 μm, 300 μm, 200 μm, or 100 μm.

3. Surface Area

The support is generally selected to have a high surface area. When calculating surface area of the support, any surface, including internal surfaces within the pores of the mesoporous material that the reactants are able to contact is typically included. Surface area of the support can be measured by techniques known in the art, for example, by nitrogen physisorption.

Typically, the support has a surface area of at least 50 $m^2/g$, at least 100 $m^2/g$, at least 200 $m^2/g$, at least 300 $m^2/g$, at least 400 $m^2/g$, at least 500 $m^2/g$, up to 1000 $m^2/g$, up to 900 $m^2/g$, up to 800 $m^2/g$, between 100 $m^2/g$ and 1000 $m^2/g$, between 200 $m^2/g$ and 1000 $m^2/g$, between 300 $m^2/g$ and 1000 $m^2/g$, between 400 $m^2/g$ and 1000 $m^2/g$, or between 500 $m^2/g$ and 1000 $m^2/g$, such as about 700 $m^2/g$.

B. Metal Oxide

The metal oxide can contain a single metal or is a mixture of metals. The metal oxide is dispersed on the surface of the support. The metal oxide may be atomically dispersed or form clusters on the surface of the support. The distribution and form of the metal oxide can be determined by any suitable method, for example X-ray absorption spectroscopy (XAS), STEM such as high-angle annular dark field-scanning transmission electron microscope (HAADF-STEM), and UV-vis (Ultraviolet-visible) spectroscopy or spectrophotometry.

In some catalysts, at least 10%, at least 20%, at least 30%, at least 40%, at least 50%, at least 60%, at least 70%, at least 80%, or at least 90% of the metal oxide is atomically dispersed on the surface of the support with the remainder of the metal oxide being in the form of clusters, as determined using statistical analysis of metal oxide structures in STEM images. For example, about 90% of the metal oxide is atomically dispersed on the surface of the support, and about 10% of the metal oxide forms clusters on the surface of the support, as determined using statistical analysis of metal oxide structures in STEM images.

1. Metals and/or Mixture of Metals

Typically, the metal or the mixture of metals is/contains a transition metal, such as an acidic early transition metal. For example, the metal oxide can contain a single metal (i.e. MOx), such as rhenium, aluminum, tungsten, or molybdenum. In some embodiments, the metal oxide contains rhenium. The metal oxide can contain a mixture of two or more metals, where at least one of the metals, and optionally both of the metals are rhenium, aluminum, tungsten, or molybdenum.

Optionally, the metal oxide contains a mixture of metals, where a first metal in the mixture of metals is selected from rhenium, aluminum, tungsten, molybdenum, and a combination thereof, and a second metal in the mixture of metals that is different from the first metal. The second metal in the mixture of metals can be rhodium, iridium, palladium, or a combination thereof. For example, the metal oxide contains a mixture of two metals (i.e. $M_2$-$M_1O_x$), where the first metal is rhenium, aluminum, tungsten, or molybdenum and the second metal is rhodium, iridium, or palladium. For example, the metal oxide can contain a mixture of two metals and where the first metal is rhenium (Re) and the second metal is rhodium (Rh), palladium (Pd), or iridium (Ir).

Optionally, the catalyst contains more than one metal oxide. Each of the metal oxides may contain a single metal or a mixture of metals. Any metal or mixture of metals described above may be used. Each of two or more metal oxides in the catalyst contains a metal that is different from the other. In some embodiments, at least one of the metal oxides contains a metal or a mixture of metals selected from the group consisting of rhenium, aluminum, tungsten, molybdenum, or a combination thereof. For example, the catalyst may contain three metal oxides, where the first metal oxide contains rhenium, the second metal oxide contains rhodium, and the third metal oxide contains a mixture of rhenium and rhodium.

2. Amount

Generally, the amount of the one metal or the total amount of two or more metals forming the metal oxide is at least 0.5 wt %, at least 1 wt %, up to 5 wt %, up to 10 wt %, at least 2 wt %, at least 3 wt % of the catalyst, at least 5 wt % of the catalyst, up to 15 wt % of the catalyst, up to 14 wt % of the catalyst, up to 13 wt %, up to 12 wt %, up to 11 wt %, up to 10.5 wt %, up to 10.2 wt %, between 0.1 wt % and 15 wt % of the catalyst, between 0.05 wt % and 10 wt %, between 0.05 wt % and 5 wt %, between 0.1 wt % and 10 wt %, between 0.1 wt % and 5 wt %, between 0.5 wt % and 10 wt %, between 0.5 wt % and 5 wt %, between 0.5 wt % and 15 wt % of the catalyst, between 1 wt % and 15 wt % of the catalyst, between 0.1 wt % and 12 wt % of the catalyst, between 0.5 wt % and 12 wt % of the catalyst, between 1 wt % and 12 wt % of the catalyst, between 0.1 wt % and 10.5 wt % of the catalyst, between 0.5 wt % and 10.5 wt % of the catalyst, or between 1 wt % and 10.5 wt % of the catalyst, or between 1 wt % and 10 wt % of the catalyst. The term "total amount of two or more metals" refers to the total weight of the two or more metals forming the metal oxide relative to the total weight of the catalyst.

For example, the catalyst contains MOx (where M represents the metal) and the amount of M forming the MOx is present in an amount of at least 0.5 wt %, at least 1 wt %, at least 2 wt %, at least 3 wt % of the catalyst, at least 5 wt % of the catalyst, up to 10 wt % of the catalyst, between 0.1 wt % and 10 wt % of the catalyst, between 0.5 wt % and 10 wt % of the catalyst, or between 1 wt % and 10 wt % of the catalyst. For example, the catalyst contains ReOx (e.g. $ReO_4$) and the amount of Re forming the ReOx is present in an amount of at least 0.5 wt %, at least 1 wt %, at least 2 wt %, at least 3 wt % of the catalyst, at least 5 wt % of the catalyst, up to 10 wt % of the catalyst, between 0.1 wt % and 10 wt % of the catalyst, between 0.5 wt % and 10 wt % of the catalyst, or between 1 wt % and 10 wt % of the catalyst.

For example, the catalyst contains a metal oxide formed from a mixture of two or more metals and the total amount of the two or more metals is present in an amount at least 0.5 wt %, at least 1 wt %, at least 2 wt %, at least 3 wt % of the catalyst, at least 5 wt % of the catalyst, up to 15 wt % of the catalyst, up to 14 wt % of the catalyst, up to 13 wt %, up to 12 wt %, up to 11 wt %, up to 10.5 wt %, up to 10.2 wt %, between 0.1 wt % and 15 wt % of the catalyst, between 0.5 wt % and 15 wt % of the catalyst, between 1 wt % and 15 wt % of the catalyst, between 0.1 wt % and 12 wt % of the catalyst, between 0.5 wt % and 12 wt % of the catalyst, between 1 wt % and 12 wt % of the catalyst, between 0.1 wt % and 10.5 wt % of the catalyst, between 0.5 wt % and 10.5 wt % of the catalyst, or between 1 wt % and 10.5 wt % of the catalyst, such as about 10.2 wt % of the catalyst.

When the catalyst contains a metal oxide formed from a mixture of two or more metals, the amount of each metal can be in a suitable range to provide a total amount of the two or more metals of at least 0.5 wt %, at least 1 wt %, at least 2 wt %, at least 3 wt % of the catalyst, at least 5 wt % of the catalyst, up to 15 wt % of the catalyst, up to 14 wt % of the catalyst, up to 13 wt %, up to 12 wt %, up to 11 wt %, up to 10.5 wt %, up to 10.2 wt %, between 0.1 wt % and 15 wt % of the catalyst, between 0.5 wt % and 15 wt % of the catalyst, between 1 wt % and 15 wt % of the catalyst, between 0.1 wt % and 12 wt % of the catalyst, between 0.5 wt % and 12 wt % of the catalyst, between 1 wt % and 12 wt % of the catalyst, between 0.1 wt % and 10.5 wt % of the catalyst, between 0.5 wt % and 10.5 wt % of the catalyst, or between 1 wt % and 10.5 wt % of the catalyst, such as about 10.2 wt % of the catalyst.

For example, the catalyst contains a metal oxide formed from a mixture of two metals (i.e. $M_2$-$M_1O_x$), where the amount of a first metal (i.e. $M_1$) forming the metal oxide can be at least 0.5 wt %, at least 1 wt %, at least 2 wt %, at least 3 wt % of the catalyst, at least 5 wt % of the catalyst, up to 10 wt % of the catalyst, in the range between 0.1 wt % and 10 wt % of the catalyst, between 0.5 wt % and 10 wt % of the catalyst, between 1 wt % and 10 wt % of the catalyst, between 2 wt % and 10 wt % of the catalyst, or between 5 wt % and 10 wt % of the catalyst; and the amount of a second metal (i.e. $M_2$) forming the metal oxide can be at least 0.05 wt %, at least 0.1 wt %, at least 0.2 wt %, at least 0.5 wt %, at least 1 wt %, up to 5 wt %, in the range between 0.05 wt % and 5 wt % of the catalyst, between 0.05 wt % and 2 wt % of the catalyst, between 0.05 wt % and 1 wt % of the catalyst, between 0.05 wt % and 0.5 wt % of the catalyst, between 0.1 wt % and 5 wt % of the catalyst, between 0.1 wt % and 2 wt % of the catalyst, between 0.1 wt % and 1 wt % of the catalyst, or between 0.1 wt % and 0.5 wt % of the catalyst.

For example, the catalyst contains a metal oxide formed from a mixture of Re and Rh, a mixture of Re and Pd, or a mixture of Re and Ir, where the amount of Re can be in the range between 0.1 wt % and 10 wt % of the catalyst, between 0.5 wt % and 10 wt % of the catalyst, between 1 wt % and 10 wt % of the catalyst, between 2 wt % and 10 wt % of the catalyst, or between 5 wt % and 10 wt % of the catalyst, such as about 10 wt % of the catalyst; and the amount of Rh, Pd, or Ir can be in the range between 0.05 wt % and 5 wt % of the catalyst, between 0.05 wt % and 2 wt % of the catalyst, between 0.05 wt % and 1 wt % of the catalyst, between 0.05 wt % and 0.5 wt % of the catalyst, between 0.1 wt % and 5 wt % of the catalyst, between 0.1 wt % and 2 wt % of the catalyst, between 0.1 wt % and 1 wt % of the catalyst, or between 0.1 wt % and 0.5 wt % of the catalyst, such as about 0.2 wt % of the catalyst.

Optionally, the catalyst contains one metal oxide and the metal oxide is present in an amount of at least 0.1 wt % of the catalyst. For example, the metal oxide is present in an amount of at least 0.5 wt %, at least 1 wt %, at least 2 wt %, at least 3 wt % of the catalyst, at least 5 wt % of the catalyst, at least 10 wt % of the catalyst, up to 30 wt % of the catalyst, up to 20 wt % of the catalyst, between 0.1 wt % and 30 wt % of the catalyst, between 1 wt % and 30 wt % of the catalyst, between 0.1 wt % and 20 wt % of the catalyst, between 1 wt % and 20 wt % of the catalyst, between 0.1 wt % and 10 wt % of the catalyst, or between 1 wt % and 10 wt % of the catalyst. For example, the metal oxide is present in an amount of between 0.1 wt % and 10 wt % of the catalyst, such as between 1 wt % and 10 wt % of the catalyst.

In some embodiments, the catalyst contains more than one metal oxide. Each of the metal oxides may be present in an amount between 0.1 wt % and 30 wt %, between 1 wt % and 30 wt % of the catalyst, between 0.1 wt % and 20 wt % of the catalyst, between 1 wt % and 20 wt % of the catalyst, between 0.1 wt % and 10 wt % of the catalyst, or between 1 wt % and 10 wt % of the catalyst. The amount of each of the metal oxides may be the same, substantially the same, or different.

Methods for preparing the disclosed catalyst are known. For example, the disclosed catalyst may be prepared using the methods described in US 2016/0199814 by Bai, et al.

II. Reactors

The disclosed catalysts can be used in a variety of reactors, for example, a gas phase plug flow reactor. Generally, a gas phase plug flow reactor includes a reaction chamber, a catalyst bed inside the reaction chamber, a gas inlet, and a gas outlet. The disclosed catalyst may be packed in the catalyst bed. The catalyst bed is at a controlled temperature. Optionally, an inert plug is located at the top and/or the bottom of the catalyst bed to maintain the catalyst bed position. Exemplary materials that are suitable for the plug include, but are not limited to, quartz wool. The gas inlet and gas outlet are in fluid communication with the reaction chamber. Typically, the gas inlet and gas outlet are configured such that a gas fed into the gas inlet, flows into the reaction chamber, through the catalyst bed packed with catalysts, and out of the catalyst bed and through the gas outlet. Optionally prior to flowing through the catalyst bed and/or after flowing through the catalyst bed, the gas passes through a plug.

Optionally, after flowing through the catalyst bed, a portion of the gas is recycled back through the reaction chamber.

An exemplary gas phase plug flow reactor 100 is shown in FIG. 8. The reactor 100 includes a reaction chamber 110. A catalyst bed 120 is inside the reaction chamber 110. Catalyst is packed in the catalyst bed 120. Two plugs 130a and 130b are placed at the top and bottom of the catalyst bed 120, respectively, to keep it in position. A gas inlet 140 is located at the top of the reaction chamber 110. A gas outlet 150 is located at the bottom of the reaction chamber 110. The gas inlet 140 and gas outlet 150 are in fluid communication with the reaction chamber 110, such that a gas fed through the gas inlet 140 into the reaction chamber 110, flows through the catalyst bed 120, and is directed from the catalyst bed 120 to the gas outlet 150.

III. Methods of Using the Catalysts

Generally, the catalysts can be used to catalyze carbonylation reactions, such as alcohol carbonylation and ester carbonylation. For example, the catalysts can be used to catalyze carbonylation of an alcohol to form its corresponding carboxylic acid, or, the catalyst can be used to catalyze carbonylation of an ester (e.g. methyl acetate) to form it corresponding anhydride (e.g. acetic anhydride). The catalytic reaction is typically a heterogeneous catalytic reaction. For example, the catalyst is solid phase and the reactants are in the liquid phase, gas phase, or both. Typically, the reaction is water-free and/or halide-free.

A. Alcohol Carbonylation

The catalysts can be used to catalyze an alcohol carbonylation reaction. The catalytic reaction is typically a heterogeneous catalytic reaction. For example, the catalyst is solid phase and the reactants are in liquid phase, gas phase, or both. Typically, the reaction is water-free and/or halide-free.

Generally, the method for alcohol carbonylation includes step (i): exposing a mixture of one or more alcohols and carbon monoxide to one of the disclosed catalysts. The one or more alcohols and carbon monoxide are reactants, and typically, are in gas phase.

As noted above, the support of the catalyst is inert and generally does not contain acidic and basic sites. The method of using the disclosed catalyst generally does not include a step of neutralizing the support prior to or during step (i). For example, the method generally does not include a step of treating the support with a basic or acidic agent, such as sodium or carbon dioxide, prior to or during step (i).

1. Contacting a Mixture of One or More Alcohols and Carbon Monoxide with the Catalyst Generally, a mixture of one or more alcohols and carbon monoxide is exposed to the catalyst by causing the one or more alcohols and carbon monoxide to flow through a catalyst bed packed with/containing at least one of the disclosed catalysts.

a. Alcohols i. Length of Carbon Chain

Typically, the one or more alcohols in the reactant mixture are C1-C20 alcohols, C1-C10 alcohols, or C1-C5 alcohols.

The alcohol may be a monohydric alcohol, R—OH, where R is a saturated aliphatic hydrocarbon group containing 1-20 carbon atoms. The saturated aliphatic hydrocarbon group can be linear, branched, or cyclic. The monohydric alcohol may be a primary alcohol, a secondary alcohol, or a tertiary alcohol.

The primary alcohol can be an alcohol having a linear saturated aliphatic hydrocarbon group, such as a methanol, ethanol, propanol, 1-butanol, 1-pentanol, 1-hexanol, 1-heptanol, 1-octanol, 1-nonanol, 1-decanol, 1-undecanol, 1-dodecanol, 1-tridecanol, 1-tetradecanol, 1-pentadecanol, 1-heptadecanol, 1-heptadecanol, 1-octadecanol, 1-nonadecanol, or 1-icosanol. For example, the alcohol is a methanol. In some embodiments, the alcohol is an ethanol or propanol.

The alcohol can also be a primary alcohol having branched saturated aliphatic hydrocarbon group, such as isobutyl alcohol.

In some embodiments, the alcohol can be a secondary alcohol, such as 2-propanol, cyclohexanol. In some embodiments, the alcohol can be a tertiary alcohol, such as a 2-methyl-2-butanol.

Optionally, the alcohol may contain more than one hydroxyl group, such as a diol, a triol, a tetraol, a pentol, a hexol, a heptol, etc. For example, the alcohol can be ethane-1,2-diol, propane-1,2-diol, propane-1,2,3-triol, butane-1,2,3,4-tetraol, pentane-1,2,3,4,5-pentol, hexane-1,2,3,4,5,6-hexol, or heptane-1,2,3,4,5,6,7-heptol.

ii. Corresponding Carboxylic Acid

Generally, the one or more alcohols in the reactant mixture are converted to their corresponding carboxylic acids. A corresponding carboxylic acid is the carboxylic acid produced from the carbonylation of a given alcohol.

Typically, an alcohol dehydrates into an alkoxy group at a dispersed site of metal oxide on the surface of the catalyst. Carbon monoxide attaches onto the alkoxy group at the surface, and produces a carboxylic acid, which is the corresponding carboxylic acid of the alcohol.

An exemplary reaction scheme for methanol carbonylation is shown in Scheme 1 and FIG. 7. For example, methanol dehydrates into methoxy group at a dispersed site of metal oxide (e.g. rhenium oxide). Carbon monoxide attaches onto the surface methoxy group and produces acetic acid, which is the corresponding carboxylic acid of methanol.

Exemplary alcohols and their corresponding carboxylic acids are listed in Table 1 below.

TABLE 1

Exemplary alcohols and their corresponding carboxylic acids

| Alcohol | Corresponding Carboxylic Acid |
|---|---|
| methanol | acetic acid |
| ethanol | propionic acid |
| propanol | butyric acid |
| 1-butanol | valeric acid |
| 1-pentanol | caproic acid |
| 1-hexanol | enanthic acid |
| 1-heptanol | caprylic acid |
| 1-octanol | pelargonic acid |
| 1-nonanol | capric acid |
| 1-decanol | undecylic acid |
| 1-undecanol | lauric acid |
| 1-dodecanol | tridecylic acid |
| 1-tridecanol | myristic acid |
| 1-tetradecanol | pentadecylic acid |
| 1-pentadecanol | palmitic acid |
| 1-heptadecanol | margaric acid |
| 1-heptadecanol | stearic acid |
| 1-octadecanol | nonadecylic acid |
| 1-nonadecanol | arachidic acid |
| 1-eicosanol | heneicosanoic acid | iii. Alcohol to Carbon Monoxide Ratio

Typically, the molar ratio of the carbon monoxide and one or more alcohols in the reactant mixture is between about 0.01 and about 100. For example, the molar ratio of the total of one or more alcohols to carbon monoxide can be at least 0.05, at least 0.1, at least 0.5, at least 1, at least 2, at least 5, up to 50, up to 40, up to 30, up to 20, up to 10, between 0.1 and 50, between 0.1 and 40, between 0.1 and 30, between 0.1 and 20, between 0.1 and 10, for example, 1. The term "total of one or more alcohols" refers to the total mole of the one or more alcohols relative to the mole of carbon monoxide.

b. Reaction Conditions

Typically, the mixture of one or more alcohols and carbon monoxide is exposed to the catalyst by causing the one or more alcohols and carbon monoxide to flow through a catalyst bed packed containing the disclosed catalyst at a controlled temperature between 100° C. and 350° C. and a pressure between 0 bar and 50 bar. The period of time that the reactant mixture is exposed to the catalyst depends on the flow rate of the reactant mixture and the geometry of the catalyst bed.

i. Reaction Temperature and Pressure

Generally, the reaction temperature for alcohol carbonylation using the disclosed catalysts is between 100° C. and 350° C., between 100° C. and 300° C., between 150° C. and 350° C., between 150° C. and 300° C., between 200° C. and 350° C., between 200° C. and 300° C., between 250° C. and 350° C., between 250° C. and 300° C., or between 220° C. and 280° C., such as about 280° C.

Generally, the reaction pressure for alcohol carbonylation using the disclosed catalysts is between 0 bar and 50 bar. For example, the reaction pressure can be up to 50 bar, up to 45 bar, up to 40 bar, up to 20 bar, up to 10 bar, up to 5 bar, up to 2 bar, up to 1 bar, up to 500 mbar, up to 200 mbar, up to 100 mbar, up to 50 mbar, up to 40 mbar, up to 35 mbar, between 0 and 50 bar, between 0 and 40 bar, between 0 and 20 bar, between 0 and 10 bar, between 0 and 1 bar, between 0 and 100 mbar, between 0 and 50 mbar, between 0 and 40 mbar, or between 0 and 35 mbar.

The alcohol carbonylation can be performed at a suitable reaction temperature, such as between 100° C. and 350° C., between 100° C. and 300° C., between 150° C. and 350° C., between 150° C. and 300° C., between 200° C. and 350° C., between 200° C. and 300° C., between 250° C. and 350° C., between 250° C. and 300° C., or between 220° C. and 280° C., and at a suitable pressure, such as a pressure up to 50 bar. In some embodiments, the alcohol carbonylation is performed at a reaction temperature between 100° C. and 350° C., between 200° C. and 350° C., or between 250° C. and 300° C., under a pressure up to 50 bar, up to 10 bar, up to 1 bar, up to 100 mbar, or up to 50 mbar. In some embodiments, the alcohol carbonylation is performed at a reaction temperature between 250° C. and 300° C., under a pressure up to 1 bar.

ii. Period of Time

The period of time that the reactant mixture is exposed to the catalyst depends on the flow rate of the reactant mixture and the geometry of the catalyst bed.

Generally, the mixture of one or more alcohols and carbon monoxide flows through the catalyst at a flow rate at least 10 mL $g_{cat}^{-1}$ $h^{-1}$, at least 20 mL $g_{cat}^{-1}$ $h^{-1}$, at least 50 mL $g_{cat}^{-1}$ $h^{-1}$, at least 100 mL $g_{cat}^{-1}$ $h^{-1}$, at least 200 mL $g_{cat}^{-1}$ $h^{-1}$, at least 500 mL $g_{cat}^{-1}$ $h^{-1}$, at least 1 L $g_{cat}^{-1}$ $h^{-1}$, at least 2 L $g_{cat}^{-1}$ $h^{-1}$, at least 3 L $g_{cat}^{-1}$ $h^{-1}$, at least 4 L $g_{cat}^{-1}$ $h^{-1}$, at least 5 L $g_{cat}^{-1}$ $h^{-1}$, up to 100 L $g_{cat}^{-1}$ $h^{-1}$, up to 50 L $g_{cat}^{-1}$ $h^{-1}$, up to 40 L $g_{cat}^{-1}$ $h^{-1}$, up to 30 L $g_{cat}^{-1}$ $h^{-1}$, up to 20 L $g_{cat}^{-1}$ $h^{-1}$, between 10 mL $g_{cat}^{-1}$ $h^{-1}$ and 40 L $g_{cat}^{-1}$ $h^{-1}$, between 10 mL $g_{cat}^{-1}$ $h^{-1}$ and 20 L $g_{cat}^{-1}$ $h^{-1}$, or between 10 mL $g_{cat}^{-1}$ $h^{-1}$ and 10 L $g_{cat}^{-1}$ $h^{-1}$, such as 5 L $g_{cat}^{-1}$ $h^{-1}$.

2. Characteristics of Catalytic Reaction

Alcohol carbonylation using the disclosed catalysts can be characterized by single-pass conversion, production rate, selectivity, and/or stability.

a. Single-Pass Conversion

The catalysts described herein can be used to increase the single-pass conversion of a given reactor relative to a catalyst containing a metal oxide dispersed on the surface of an acidic support (e.g., zirconium dioxide ($ZrO_2$)) or a basic support (e.g., magnesium oxide (MgO)) at a temperature in the range of 100° C. to 350° C. and a pressure from 0 bar to 50 bar, such as up to 1 bar. For example, an alcohol flowing through a catalyst bed packed with Rh/ZrO2 catalyst, which contains sodium that neutralizes the ZrO2 support, was shown to have a single pass conversion of about 0.5% at a temperature of 300° C. and a pressure of 1 bar. Similarly, an alcohol flowing through a catalyst bed packed with Re/MgO catalyst, was shown to have a single pass conversion of about 0.2% at a temperature of 245° C. and a pressure of 1 bar.

In contrast, when fed into a reactor containing one or more of the catalysts disclosed herein, the alcohol in the reactant mixture can have a single pass conversion of 10% or higher, such as 20% or higher, 30% or higher, 40% or higher, 50% or higher, or 60% or higher, optionally from 10% to 70%, from 10% to 50%, or from 30% to 50%, optionally from 50% to 70%, from 50% to 65%, or from 50% to 60%.

The single-pass conversion for a given reactant can be calculated using Formula (1):

Single-pass conversion=
(reactant$_{reactor\ feed}$−reactant$_{reactor\ outlet}$)/
(reactant$_{reactor\ feed}$)×100

Generally, an alcohol carbonylation reaction conducted in a reactor containing one or more of the catalysts disclosed herein has a single-pass conversion of at least 10%, at least 15%, at least 20%, at least 25%, at least 30%, at least 35%, at least 40%, at least 45%, at least 50%, at least 55%, or at least 60% for the alcohol in the reactant mixture.

For example, an alcohol flowing through a catalyst bed packed with the disclosed catalysts can have a single-pass conversion of at least 50% at a temperature between 200° C. and 300° C. and a pressure up to 1 bar.

b. Production Rate

The production rate in alcohol carbonylation reactions refers to the amount of corresponding carboxylic acid generated in a given period of time. The production rate may increase with an increase in the temperature at which the reaction is carried out.

The production rate in an alcohol carboynlation reaction is at least substantially equivalent to typical production rates for industrial processes involving liquid phase halogen alcohol carbonylation reactions, which typically have a production rate of 1.5 mmol dm$^{-3}$ s$^{-1}$ (Maths, et al., *Dalton Trans.*, 1996, 2187-2196). Comparison of the acetic acid production rate in an alcohol carbonylation reaction using the disclosed catalysts and exemplary known heterogamous and homogeneous systems is shown in Table 4.

Generally, alcohol carbonylation using the disclosed catalysts has a production rate of at least 0.007 mmol s$^{-1}$ g$_{metal}^{-1}$, at least 0.01 mmol s$^{-1}$ g$_{metal}^{-1}$, at least 0.02 mmol s$^{-1}$ g$_{metal}^{-1}$, at least 0.03 mmol s$^{-1}$ g$_{metal}^{-1}$, at least 0.04 mmol s$^{-1}$ g$_{metal}^{-1}$, at least 0.05 mmol s$^{-1}$ g$_{metal}^{-1}$, at least 0.1 mmol s$^{-1}$ g$_{metal}^{-1}$, at least 0.15 mmol s$^{-1}$ g$_{metal}^{-1}$, at least 0.16 mmol s$^{-1}$ g$_{metal}^{-1}$, at least 0.17 mmol s$^{-1}$ g$_{metal}^{-1}$, at least 0.18 mmol s$^{-1}$ g$_{metal}^{-1}$, at least 0.19 mmol s$^{-1}$ g$_{metal}^{-1}$, or at least 0.2 mmol s$^{-1}$ g$_{metal}^{-1}$, at a reaction temperature ranging from 100° C. to 350° C. and a pressure of 0 bar and 50 bar.

In some embodiments, alcohol carbonylation using the disclosed catalysts has a production rate of at least 0.007 mmol s$^{-1}$ g$_{metal}^{-1}$, at least 0.01 mmol s$^{-1}$ g$_{metal}^{-1}$, at least 0.02 mmol s$^{-1}$ g$_{metal}^{-1}$, at least 0.03 mmol s$^{-1}$ g$_{metal}^{-1}$, at least 0.04 mmol s$^{-1}$ g$_{metal}^{-1}$, at least 0.05 mmol s$^{-1}$ g$_{metal}^{-1}$, at least 0.1 mmol s$^{-1}$ g$_{metal}^{-1}$, at least 0.15 mmol s$^{-1}$ g$_{metal}^{-1}$, at least 0.16 mmol s$^{-1}$ g$_{metal}^{-1}$, at least 0.17 mmol s$^{-1}$ g$_{metal}^{-1}$, at least 0.18 mmol s$^{-1}$ g$_{metal}^{-1}$, at least 0.19 mmol s$^{-1}$ g$_{metal}^{-1}$, or at least 0.2 mmol s$^{-1}$ g$_{metal}^{-1}$, at a reaction temperature ranging from 200° C. to 350° C., 200° C. to 300° C., or 250° C. to 300° C. and a pressure up to 1 bar.

For example, the alcohol carbonylation using the disclosed catalysts has a production rate of at least 0.17 mmol s$^{-1}$ g$_{metal}^{-1}$, such as about 0.2 mmol s$^{-1}$ g$_{metal}^{-1}$ (about 1.8 mmol dm$^{-3}$ s$^{-1}$), at a reaction temperature ranging from 200° C. to 350° C., 200° C. to 300° C., or 250° C. to 300° C. and a pressure of up to 50 bar, up to 10 bar, or up to 1 bar in gas phase and halide-free alcohol carbonylation reactions.

Optionally, a catalyst containing a metal oxide formed from a mixture of metals, such as a mixture of rhenium and rhodium, a mixture of rhenium and palladium, or a mixture of rhenium and iridium, can increase the corresponding carboxylic acid production rate by at least 2 times, at least 5 times, or at least an order of magnitude when compared with the carboxylic acid production rate using a catalyst containing a metal oxide formed from a single metal, for the same alcohol carbonylation reaction. For example, a catalyst containing Rh—Re-Ox can increase the corresponding carboxylic acid production rate by at least an order of magnitude compared with a catalyst containing ReOx only, for the same alcohol carbonylation reaction.

c. Selectivity

The alcohol carbonylation using the disclosed catalysts may produce more than one product. For example, methanol carbonylation using the disclosed catalysts may produce acetic acid, and byproducts, such as dimethyl ether, methyl acetate, and/or formaldehyde.

For example, dimethyl ether may be formed from methanol reacting with surface methoxy group and/or combination of two surface methoxy groups. Dimethyl ether may react with surface acetyl moiety, which is produced by CO insertion onto surface methyoxy group, to form methyl acetate. Formaldehyde may be formed from methoxy dehydration.

Typically, the production rate of a corresponding carboxylic acid is at least 2 times, at least 5 times, at least 10 times, at least 20 times, at least 30 times, at least 40 times, at least 45 times, at least 50 times, at least 55 times, at least 60 times, at least 65 times, at least 70 times, at least 75 times, or at least 80 times higher than the production rate of a byproduct under the same reaction temperature, reaction pressure, and flow rate.

The catalyst selectivity in alcohol carbonylation reactions generally refers to the percentage of alcohol that is converted into the corresponding carboxylic acid.

Typically, the catalyst selectivity for producing the corresponding carboxylic acid in an alcohol carbonylation is high, such as at least 50%, at least 55%, at least 60%, at least 65%, at least 70%, at least 75%, at least 80%, at least 85%, at least 90%, or at least 95%, at a reaction temperature ranging from 100° C. to 350° C. and a pressure of 0 bar and 50 bar. In some embodiments, the catalyst selectivity for producing the corresponding carboxylic acid in an alcohol carbonylation is at least 80%, at least 85%, or at least 90%, at a reaction temperature ranging from 200° C. to 350° C., 200° C. to 300° C., or 250° C. to 300° C. and a pressure up to 1 bar. For example, the selectivity to acetic acid in a methanol carbonylation using the disclosed catalyst is at least 80%, at least 85%, or at least 90%, such as at least 93% or 95%, at a reaction temperature ranging from 200° C. to 350° C., 200° C. to 300° C., or 250° C. to 300° C. and a pressure of up to 50 bar, up to 10 bar, or up to 1 bar in gas phase and halide-free alcohol carbonylation reactions.

Optionally, a catalyst containing a metal oxide formed from a mixture of metals, such as a mixture of rhenium and rhodium, a mixture of rhenium and palladium, or a mixture of rhenium and iridium, can increase the selectivity for producing the corresponding carboxylic acid by at least 0.2%, at least 0.5%, at least 1%, at least 2%, at least 5%, up to 10%, from 0.2% to 10%, from 0.5% to 10%, from 1% to 10%, from 2% to 10%, or from 5% to 10%, when compared with the selectivity for producing the corresponding carboxylic acid using a catalyst containing a metal oxide formed from a single metal, for the same alcohol carbonylation reaction. For example, a catalyst containing Rh—Re-Ox can increase the selectivity for producing the corresponding carboxylic acid by at least 0.2%, at least 0.5%, at least 1%, at least 2%, at least 5%, up to 10%, from 0.2% to 10%, from 0.5% to 10%, from 1% to 10%, from 2% to 10%, or from 5% to 10%, compared with a catalyst containing ReOx only, for the same alcohol carbonylation reaction.

Optionally, a catalyst containing a metal oxide formed from a mixture of metals, such as a mixture of rhenium and rhodium, a mixture of rhenium and palladium, or a mixture of rhenium and iridium, can increase the corresponding carboxylic acid production rate by at least 2 times, at least 5 times, or at least an order of magnitude and increase the selectivity for producing the carboxylic acid by at least 0.2%, at least 0.5%, or at least 1% when compared with the carboxylic acid production rate using a catalyst containing a metal oxide formed from a single metal, for the same alcohol carbonylation reaction. For example, a catalyst containing Rh—Re-Ox can increase the corresponding carboxylic acid production rate by at least an order of magnitude and increase the selectivity for producing the corresponding carboxylic acid by at least 0.2%, at least 0.5%, at least 1%, at least 2%, at least 5%, up to 10%, from 0.2% to 10%, from 0.5% to 10%, from 1% to 10%, from 2% to 10%, or from 5% to 10%, compared with a catalyst containing ReOx only, for the same alcohol carbonylation reaction.

d. Stability

Catalyst stability generally refers to the catalyst's performance under reaction conditions without any observable decrease in the reactivity or selectivity of the catalyst. For example, the stability is measured as a less than 10% decrease, in the reactivity or selectivity of the catalyst, calculated as exemplified in the examples below.

Typically, the disclosed catalysts are stable for at least 40 hours, at least 50 hours, or at least 60 hours at a temperature between 100° C. and 350 and a pressure between 0 bar and 50 bar. For example, there is no observable decrease in reactivity and selectivity of the disclosed catalysts at a temperature between 100° C. and 350° C. and a pressure between 0 bar and 50 bar in an alcohol carbonylation reaction for at least 40 hours, at least 50 hours, or at least 60 hours.

In some embodiments, the disclosed catalysts are stable for at least 40 hours, at least 50 hours, or at least 60 hours at a reaction temperature ranging from 200° C. to 350° C., 200° C. to 300° C., or 250° C. to 300° C. and a pressure up to up to 50 bar, up to 10 bar, or up to 1 bar. For example, the disclosed catalysts are stable for at least 40 hours, at least 50 hours, or at least 60 hours at a reaction temperature ranging from 200° C. to 350° C. and a pressure up to 1 bar.

3. Optional Steps a. Bubbling the One or More Alcohols with an Inert Gas

The method optionally includes a step of bubbling the one or more alcohols with an inert gas prior to step (i). Generally, the inert gas is used as a diluent to control the partial pressure of the alcohol, and thus, the concentration of the alcohol.

Optionally, the reactant mixture contains a single alcohol, and the alcohol is bubbled with an inert gas prior to step (i) (i.e., the step of exposing a mixture of one or more alcohols and carbon monoxide to at least one of the disclosed catalyst (which include a support)).

In some embodiments, the reactant mixture includes more than one alcohol. Optionally, when more than one alcohol is used, each of the alcohols is bubbled separately with an inert gas to control their individual partial pressure. Each of the alcohols may have the same, substantially the same, or different partial pressures. Optionally, two or more of the alcohols have a same or similar first partial pressure, and one or more alcohols have a second partial pressure that is different than that of the first partial pressure.

Alternatively, two or more of the alcohols having a same or similar first partial pressure may be bubbled together as a first group, and one or more alcohols having a second partial pressure that is different from the first partial pressure may be bubbled together as a second group.

Optionally, each of the alcohols have the same partial pressure and are bubbled together with an inert gas.

Examples of suitable inert gas for bubbling the one or more alcohols include, helium, neon, argon, krypton, xenon, radon, and nitrogen. For example, the inert gas for bubbling the one or more alcohols is argon or nitrogen.

b. Feeding the One or More Alcohols by a Pump

The method optionally includes a step of bubbling/feeding the one or more alcohols into a reactor containing the disclosed catalysts by a pump prior to step (i).

Optionally, a single alcohol is fed into the reactor by a pump and mixed with the carbon monoxide to form the reactant mixture prior to step (i). Alternatively, a single alcohol is mixed with the carbon monoxide to form a reactant mixture and the reactant mixture is fed into the reactor by a pump prior to step (i).

In some embodiments, the reactant mixture includes more than one alcohol. Optionally, each of the alcohols is fed separately into the reactor by a pump, and mixed with the carbon monoxide to form the reactant mixture prior to step (i). The one or more alcohols can be fed simultaneously, substantially simultaneously, or sequentially into the reactor. Each of the alcohols may be pumped into the reactor at the same, substantially the same, or different pressures. Optionally, the alcohols are mixed and fed into the reactor by a pump as a group at the same pressure, and mixed with the carbon monoxide in the reactor to form the reactant mixture prior to step (i). Optionally, the alcohols are mixed together and mixed with the carbon monoxide to form the reactant mixture, then are fed into the reactor by a pump at the same pressure prior to step (i).

Optionally, two or more of the alcohols are mixed and are fed together as a first group into the reactor by a first pump, and one or more alcohols are fed separately as a second group into the reactor by a second pump. The first group and second group can be fed simultaneously, substantially simultaneously, or sequentially into the reactor. The first group and second group may be pumped into the reactor at the same, substantially the same, or different pressures. Optionally, the carbon monoxide can mix with the first group and/or the second group before feeding into the reactor. Optionally, the carbon monoxide can mix with the first and/or the second group in the reactor.

c. Treat the Metal Oxide

The method may include a step of exposing the catalyst to an oxidizing gas to oxidize the metal oxide prior to step (i).

Typically, the method does not include a step of neutralizing the support prior to or during step (i). For example, the method does not include a step of treating the support with a basic or acidic agent, such as sodium or carbon dioxide, prior to or during step (i).

i. Oxidize the Metal Oxide

Optionally, prior to step (i), the catalyst is exposed to an oxidizing gas to oxidize the metal oxide. The oxidizing gas is a suitable gas to oxidize the metal oxide in the catalyst. The oxidizing gas is able to oxidize the metal oxide such that the metal of the metal oxide reaches a higher oxidation state.

Examples of suitable oxidizing gases for oxidizing the metal oxide include, but are not limited to, oxygen and air. For example, the oxidizing gas is oxygen.

(1) Oxidation Temperature

Generally, the metal oxide is oxidized with an oxidizing gas at a temperature at least 200° C., at least 250° C., at least 300° C., at least 350° C., up to 600° C., up to 550° C., up to 500° C., up to 450° C., up to 400° C., between 200° C. and 400° C., between 250° C. and 400° C., or between 300° C. and 400° C., such as 300° C. to 350° C.

(2) Period of Time for Oxidation

Generally, the metal oxide is treated with an oxidizing gas for a time period of at least 10 minutes, at least 20 minutes, at least 30 minutes, at least 40 minutes, at least 50 minutes, at least 1 hour, up to 5 hours, up to 4 hours, up to 3 hours, up to 2 hours, between 10 minutes and 2 hours, or between 30 minutes and 2 hours, such as 30 minutes to 1 hour.

ii. Oxidize then Reduce the Metal Oxide

Optionally, the metal oxide in the catalyst is oxidized with an oxidizing agent and then the oxidized metal oxide is reduced with a reducing gas prior to step (i).

The reducing gas is a suitable gas to reduce the metal oxide or the oxidized metal oxide in the catalyst. A reducing gas reduces the metal oxide such that the metal of the metal oxide reaches a lower oxidation state.

Examples of a suitable reducing gas include, but are not limited to, hydrogen, carbon monoxide, ammonia, methane, and nitric oxide. For example, the reducing gas is carbon monoxide.

The metal oxide can be first oxidized with any oxidizing gas described above. The oxidation temperature and period of time can be any oxidation temperature and time period described above.

(1) Reduction Temperature

With respect to reduction, the reduction temperature can be at least 150° C., at least 200° C., at least 250° C., up to 450° C., up to 400° C., up to 350° C., up to 300° C., between 150° C. and 300° C., or between 200° C. and 300° C., such as 250° C. to 300° C. Typically, the reduction temperature is lower than the oxidation temperature. For example, the metal oxide can be oxidized at 350° C. and then reduced at 250° C.

(2) Period of Time for Reduction

The period of time for reduction can be the same, substantially the same, or different than the period of time for oxidation. For example, the period of time for reduction is the same or substantially the same as the period of time for oxidation, such as 1 hour. Optionally, the period of time for reduction is different from the period of time for oxidation. The period of time for reduction may be the longer or shorter than the period of time for oxidation.

d. Recycle Gas Streams

The method may include a step of recycling the gas stream after step (i). Gas streams released from the gas outlet may contain a portion of the reactant mixture, which is a mixture of unreacted alcohols and carbon monoxide after passing the catalyst bed.

A gas stream containing unreacted alcohols and carbon monoxide that is released from the gas outlet may be returned to the reaction chamber via the gas inlet, flow through the catalyst bed for a second time, and then flow from the catalyst bed through the gas outlet.

Optionally, the recycling step is repeated at least 1 time, at least 2 times, at least 3 times, at least 4 times, at least 5 times, at least 6 times, at least 7 times, at least 8 times, etc.

Optionally, a sensor located at or near the gas outlet measures the concentration of unreacted alcohols and/or carbon monoxide in the gas stream released from the gas outlet. Optionally, the recycling step is repeated until the sensor measures a concentration of unreacted alcohols and/or carbon monoxide in the released gas stream below a threshold value. For example, the threshold value is up to 20%, up to 15%, up to 10%, up to 5%, up to 2%, or up to 1% of the alcohol and/or carbon monoxide concentration in a fresh reactant mixture (before flowing through the catalyst bed packed with catalysts).

B. Catalyze Ester Carbonylation

The disclosed catalysts can be used to catalyze an ester carbonylation reaction. Typically, the method of catalyzing ester carbonylation follows the method step described above. For example, the method includes step (i): exposing a mixture of one or more esters and carbon monoxide to at least one of the disclosed catalysts. The one or more esters and carbon monoxide are reactants, and typically, are in gas phase.

The method of using the disclosed catalysts for catalyzing ester carbonylation generally does not include a step of neutralizing the support prior to or during step (i). For example, the method generally does not include a step of treating the support with a basic or acidic agent, such as sodium or carbon dioxide, prior to or during step (i).

Optionally, the method of using the disclosed catalysts for catalyzing ester carbonylation can include any or all of the optional steps described above for alcohol carbonylation, modified to replace the one or more alcohols with one or more esters. For example, the user can bubble the one or more esters with an inert gas prior to step (i), feed the one or more esters into a reactor containing the disclosed catalysts by a pump prior to step (i), exposing the catalyst to an oxidizing gas to oxidize the metal oxide prior to step (i), and/or recycle the gas stream containing unreacted esters and/or carbon monoxide after step (i).

1. Expose Mixture of One or More Esters and Carbon Monoxide to the Catalyst

With respect to step (i) for ester carbonylation, the mixture of one or more esters and carbon monoxide is exposed to the catalyst by causing the the mixture of one or more esters and carbon monoxide to flow through a catalyst bed packed containing the disclosed catalyst.

a. Esters and Corresponding Anhydrides

Typically, the one or more esters in the reactant mixture are methyl esters, such as methyl acetate, methyl propionate, and methyl butyrate. The one or more esters are converted to their corresponding anhydride. A corresponding anhydride is the anhydride produced from the carbonylation of a given ester.

Typically, a methyl ester is activated to a methyl and an acyl group on the active site of the catalyst and followed by CO insertion into the methyl group. The surface —$CH_3$— CO reacts with surface bound acyl species to produce a corresponding anhydride. For example, carbonylation of methyl acetate produces acetic anhydride; carbonylation of methyl propionate produces acetic propionic anhydride; and carbonylation of methyl butyrate produces acetic butyric anhydride.

An exemplary reaction scheme for methanol carbonylation is shown in Scheme 2. For example, methyl acetate is activated to methyl and acetyl on $ReO_4$ followed by CO insertion into the methyl group. The surface —$CH_3$—CO reacts with —O—(CO)—$CH_3$ species to produce acetic anhydride.

b. Ester to Carbon Monoxide Ratio

Typically, the molar ratio of the carbon monoxide and one or more esters in the reactant mixture is between about 0.01 and about 100. For example, the molar ratio of the total of one or more esters to carbon monoxide can be at least 0.05, at least 0.1, at least 0.5, at least 1, at least 2, at least 5, up to 50, up to 40, up to 30, up to 20, up to 10, between 0.1 and 50, between 0.1 and 40, between 0.1 and 30, between 0.1 and 20, between 0.1 and 10, for example, 1. The term "total of one or more esters" refers to the total mole of the one or more esters relative to the mole of carbon monoxide.

c. Reaction Conditions

Typically, the mixture of one or more esters and carbon monoxide is exposed to the catalyst by flowing through a catalyst bed packed containing the disclosed catalyst at a controlled temperature between 100° C. and 350° C. and a pressure between 0 bar and 50 bar. The period of time that the reactant mixture is exposed to the catalyst depends on the flow rate of the reactant mixture and the geometry of the catalyst bed.

i. Reaction Temperature and Pressure

Generally, the reaction temperature for ester carbonylation using the disclosed catalysts is between 100° C. and 350° C., between 100° C. and 300° C., between 150° C. and 350° C., between 150° C. and 300° C., between 200° C. and 350° C., between 200° C. and 300° C., between 250° C. and 350° C., between 250° C. and 300° C., or between 220° C. and 280° C., such as about 240° C., about 260° C., or about 280° C.

Generally, the reaction pressure for ester carbonylation using the disclosed catalysts is between 0 bar and 50 bar. For example, the reaction pressure for ester carbonylation using the disclosed catalyst is up to 50 bar, up to 40 bar, up to 20 bar, up to 10 bar, up to 5 bar, up to 2 bar, up to 1 bar, up to 500 mbar, up to 400 mbar, up to 300 mbar, up to 200 mbar, between 0 and 50 bar, between 0 and 40 bar, between 0 and 20 bar, between 0 and 10 bar, between 0 and 5 bar, between 0 bar and 1 bar, between 0 and 500 mbar, between 0 and 400 mbar, between 0 and 300 mbar, or between 0 and 200 mbar, such as about 177 mbar.

Ester carbonylation using the disclosed catalysts can be performed at a suitable reaction temperature, such as between 100° C. and 350° C., between 100° C. and 300° C., between 150° C. and 350° C., between 150° C. and 300° C., between 200° C. and 350° C., between 200° C. and 300° C., between 250° C. and 350° C., between 250° C. and 300° C., or between 220° C. and 280° C., such as about 240° C., about 260° C., or about 280° C. and at a suitable pressure, such as a pressure up to 50 bar. In some embodiments, the ester carbonylation is performed at a reaction temperature between 100° C. and 350° C., between 200° C. and 350° C., between 220° C. and 300° C., or between 220° C. and 280° C., under a pressure of up to 1 bar, up to 500 mbar, up to 200 mbar, between 0 bar and 1 bar, between 0 and 500 mbar, between 0 and 400 mbar, between 0 and 300 mbar, or between 0 and 200 mbar. In some embodiments, the ester carbonylation is performed at a reaction temperature between 220° C. and 280° C., such as about 240° C., about 260° C., or about 280° C., under a pressure up to 1 bar, such as about 177 mbar.

ii. Period of Time

The period of time that the ester(s) and carbon monoxide are exposed to the catalyst depends on the flow rate of the reactant mixture and the geometry of the catalyst bed.

Generally, the mixture of one or more esters and carbon monoxide flows through the catalyst at a flow rate at least 10 mL $g_{cat}^{-1}$ $h^{-1}$, at least 20 mL $g_{cat}^{-1}$ $h^{-1}$, at least 50 mL $g_{cat}^{-1}$ $h^{-1}$, at least 100 mL $g_{cat}^{-1}$ $h^{-1}$, at least 200 mL $g_{cat}^{-1}$ $h^{-1}$, at least 500 mL $g_{cat}^{-1}$ $h^{-1}$, at least 1 L $g_{cat}^{-1}$ $h^{-1}$, at least 2 L $g_{cat}^{-1}$ $h^{-1}$, at least 3 L $g_{cat}^{-1}$ $h^{-1}$, at least 4 L $g_{cat}^{-1}$ $h^{-1}$, at least 5 L $g_{cat}^{-1}$ $h^{-1}$, up to 100 L $g_{cat}^{-1}$ $h^{-1}$, up to 50 L $g_{cat}^{-1}$ $h^{-1}$, up to 40 L $g_{cat}^{-1}$ $h^{-1}$, up to 30 L $g_{cat}^{-1}$ $h^{-1}$, up to 20 L $g_{cat}^{-1}$ $h^{-1}$, between 10 mL $g_{cat}^{-1}$ $h^{-1}$ and 40 L $g_{cat}^{-1}$ $h^{-1}$, between 10 mL $g_{cat}^{-1}$ $h^{-1}$ and 20 L $g_{cat}^{-1}$ $h^{-1}$, or between 10 mL $g_{cat}^{-1}$ $h^{-1}$ and 10 L $g_{cat}^{-1}$ $h^{-1}$, such as 5 L $g_{cat}^{-1}$ $h^{-1}$.

2. Characteristics of Catalytic Reaction

Typically, the method of catalyzing ester carbonylation using the disclosed catalysts can be characterized by single-pass conversion, production rate, selectivity, and/or stability as described above. For example, there is no observable decrease in reactivity and selectivity of the disclosed catalysts at a temperature between 100° C. and 350° C. and a pressure between 0 bar and 50 bar in an ester carbonylation reaction for at least 40 hours, at least 50 hours, or at least 60 hours.

a. Single-Pass Conversion

With respect to single-pass conversion, when fed into a reactor, containing one or more of the catalysts disclosed herein, the ester(s) in the reactant mixture can have a single pass conversion of 0.1% or higher, such as 0.2% or higher, 0.5% or higher, 1% or higher, 2% or higher, 3% or higher, 4% or higher, 5% or higher, 6% or higher, 7% or higher, 8% or higher, or 9% or higher, optionally from 0.1% to 10%, from 0.5% to 9%, or from 1% to 9%, from 2% to 9%, from 3% to 9%, from 4% to 9%, or from 5% to 9%.

Generally, an ester carbonylation reaction conducted in a reactor containing one or more of the catalysts disclosed herein has a single-pass conversion of at least 0.5%, at least 1%, at least 2%, at least 3%, at least 4%, at least 5%, at least 6%, at least 7%, at least 9%, or from 0.5% to 9% for the ester in the reactant mixture.

For example, an ester flowing through a catalyst bed packed with the disclosed catalysts can have a single-pass conversion of at least 0.5% or from 0.5% to 9% at a temperature between 200° C. and 300° C. and a pressure up to 1 bar, such as between 240° C. and 280° C. and a pressure up to 200 mbar.

b. Production Rate

With respect to the production rate in ester carbonylation reactions, it refers to the amount of corresponding anhydride generated in a given period of time. The production rate may increase with an increase in temperature.

Generally, ester carbonylation using the disclosed catalysts has a production rate of at least 0.0004 mmol $s^{-1}$ $g_{metal}^{-1}$, at least 0.0005 mmol $s^{-1}$ $g_{metal}^{-1}$, at least 0.0006 mmol $s^{-1}$ $g_{metal}^{-1}$, at least 0.0007 mmol least 0.0008 mmol $s^{-1}$ $g_{metal}^{-1}$, at least 0.0009 mmol $s^{-1}$ $g_{metal}^{-1}$, at least 0.001 mmol $s^{-1}$ $g_{metal}^{-1}$, at least 0.0015 mmol $s^{-1}$ $g_{metal}^{-1}$, at least 0.0016 mmol $s^{-1}$ $g_{metal}^{-1}$, at least 0.0017 mmol $s^{-1}$ $g_{metal}^{-1}$, at least 0.0018 mmol $s^{-1}$ $g_{metal}^{-1}$, at least 0.0019 mmol $s^{-1}$ $g_{metal}^{-1}$, at least 0.002 mmol $s^{-1}$ $g_{metal}^{-1}$, at least 0.0022 mmol $s^{-1}$ $g_{metal}^{-1}$, at least 0.0024 mmol $s^{-1}$ $g_{metal}^{-1}$, at least 0.0026 mmol $s^{-1}$ $g_{metal}^{-1}$, at least 0.0028 mmol $s^{-1}$ $g_{metal}^{-1}$, from 0.0004 mmol $s^{-1}$ $g_{metal}^{-1}$ to 0.0028 mmol $s^{-1}$ $g_{metal}^{-1}$, from 0.0005 mmol $s^{-1}$ $g_{metal}^{-1}$ to 0.0028 mmol $g_{metal}^{-1}$, from 0.0006 mmol $s^{-1}$ $g_{metal}^{-1}$ to 0.0028 mmol $s^{-1}$ $g_{metal}^{-1}$, from 0.0008 mmol $s^{-1}$ $g_{metal}^{-1}$ to 0.0028 mmol $s^{-1}$ $g_{metal}^{-1}$, or from 0.001 mmol $s^{-1}$ $g_{metal}^{-1}$ to 0.0028 mmol $s^{-1}$ $g_{metal}^{-1}$, at a reaction temperature ranging from 100° C. to 350° C. and a pressure of 0 bar and 50 bar.

In some embodiments, ester carbonylation using the disclosed catalysts has a production rate of at least 0.0004 mmol $s^{-1}$ $g_{metal}^{-1}$, at least 0.0007 mmol $s^{-1}$ $g_{metal}^{-1}$, at least 0.001 mmol $s^{-1}$ $g_{metal}^{-1}$, at least 0.0015 mmol $s^{-1}$ $g_{metal}^{-1}$, at least 0.002 mmol $s^{-1}$ $g_{metal}^{-1}$, at least 0.0022 mmol $s^{-1}$ $g_{metal}^{-1}$, at least 0.0024 mmol $s^{-1}$ $g_{metal}^{-1}$, at least 0.0026 mmol $s^{-1}$ $g_{metal}^{-1}$, at least 0.0028 mmol $s^{-1}$ $g_{metal}^{-1}$, or from 0.0004 mmol $s^{-1}$ $g_{metal}^{-1}$ to 0.0028 mmol $s^{-1}$ $g_{metal}^{-1}$, at a reaction temperature ranging from 200° C. to 350° C., 200° C. to 300° C., or 240° C. to 280° C. and a pressure up to 1 bar.

For example, the ester carbonylation using the disclosed catalysts has a production rate of at least 0.0004 mmol $s^{-1}$ $g_{metal}^{-1}$, such as about 0.0028 mmol $s^{-1}$ $g_{metal}^{-1}$, at a reaction temperature ranging from 200° C. to 350° C., 200° C. to 300° C., or 240° C. to 280° C. and a pressure of up to 1 bar or up to 200 mbar, such as about 177 mbar, in gas phase and halide-free ester carbonylation reactions.

c. Selectivity

The ester carbonylation using the disclosed catalysts may produce more than one product. For example, methyl acetate carbonylation using the disclosed catalysts may produce acetic anhydride and byproducts (e.g. acetic acid and hydrocarbons).

Typically, the production rate of a corresponding anhydride from an ester is at least 2 times, at least 5 times, at least 10 times, at least 20 times, at least 30 times, at least 40 times, at least 45 times, at least 50 times, at least 55 times, at least 60 times, at least 65 times, at least 70 times, at least 75 times, or at least 80 times higher than the production rate of a byproduct under the same reaction temperature, reaction pressure, and flow rate.

With respect to the catalyst selectivity in ester carbonylation reactions, it refers to the percentage of ester that is converted into the corresponding anhydride.

Typically, the catalyst selectivity for producing the corresponding anhydride in an ester carbonylation is at least 10%, at least 12%, at least 15%, at least 17%, at least 18%, at least 19%, at least 20%, at least 21%, at least 22%, from 15% to 25%, from 15% to 22%, or from 17% to 22%. In some embodiments, the catalyst selectivity for producing the corresponding anhydride in an ester carbonylation is at least 10%, at least 15%, at least 17%, from 15% to 25%, or from 17% to 22%, at a reaction temperature ranging from 200° C. to 350° C., 200° C. to 300° C., or 240° C. to 280° C. and a pressure of up to 1 bar or up to 200 mbar. For example, the selectivity to acetic anhydride in a methyl acetate carbonylation using the disclosed catalyst is at least 15%, at least 17%, from 15% to 25%, or from 17% to 22%, at a reaction temperature ranging from 200° C. to 350° C., 200° C. to 300° C., or 240° C. to 280° C. and a pressure of up to 1 bar or up to 200 mbar, such as about 177 mbar.

The disclosed catalysts and methods can be further understood through the following numbered paragraphs.

1. A catalyst comprising
   a support; and
   a metal oxide,
   wherein the metal oxide is dispersed on the surface of the support.
2. The catalyst of paragraph 1, wherein at least 10% of the metal oxide is atomically dispersed on the surface of the support.
3. The catalyst of paragraph 1 or paragraph 2, wherein the support comprises a chemically inert material.
4. The catalyst of any one of paragraphs 1-3, wherein the support comprises a mesoporous material or a microporous material.
5. The catalyst of paragraph 4, wherein the support comprises mesoporous material and the mesoporous material has an average pore diameter of at least 1 nm, at least 2 nm, at least 3 nm, at least 4 nm, up to 50 nm, up to 40 nm, up to 30 nm, up to 20 nm, up to 10 nm, between 1 nm and 40 nm, between 1 nm and 30 nm, between 1 nm and 20 nm, between 1 nm and 15 nm, or between 1 nm and 10 nm.
6. The catalyst of paragraph 4, wherein the support comprises a microporous material and the microporous material has an average pore diameter of up to 1 nm, up to 0.9 nm, up to 0.8 nm, up to 0.7 nm, at least 0.4 nm, at least 0.5 nm, between 0.4 nm and 1 nm, between 0.5 nm and 1 nm, between 0.4 nm and 0.9 nm, or between 0.4 nm and 0.8 nm.
7. The catalyst of any one of paragraphs 1-6, wherein the support has a surface area of at least 50 $m^2/g$, at least 100 $m^2/g$, at least 200 $m^2/g$, at least 300 $m^2/g$, at least 400 $m^2/g$, at least 500 $m^2/g$, up to 1000 $m^2/g$, up to 900 $m^2/g$, up to 800 $m^2/g$, between 100 $m^2/g$ and 1000 $m^2/g$, between 200 $m^2/g$ and 1000 $m^2/g$, between 300 $m^2/g$ and 1000 $m^2/g$, between 400 $m^2/g$ and 1000 $m^2/g$, or between 500 $m^2/g$ and 1000 $m^2/g$.
8. The catalyst of any one of paragraphs 1-7, wherein the support comprises silicon dioxide or a carbon-based material.
9. The catalyst of any one of paragraphs 1-8, wherein the support is in the form of a sheet or nanoparticle, preferably wherein the support is silicon dioxide.
10. The catalyst of paragraph 8, wherein the carbon-based material is activated carbon, carbon nanotubes, carbon black, or graphene.
11. The catalyst of any one of paragraphs 1-10, wherein the metal oxide comprises a first metal selected from the group consisting of rhenium, aluminum, tungsten, and molybdenum.
12. The catalyst of any one of paragraphs 1-11, wherein the metal oxide comprises rhenium.
13. The catalyst of paragraph 11 or paragraph 12, wherein the first metal is present in an amount of at least 0.5 wt %, at least 1 wt %, at least 2 wt %, at least 3 wt % of the catalyst, at least 5 wt % of the catalyst, up to 10 wt % of the catalyst, in the range between 0.1 wt % and 10 wt % of the catalyst, between 0.5 wt % and 10 wt % of the catalyst, between 1 wt % and 10 wt % of the catalyst, between 2 wt % and 10 wt % of the catalyst, or between 5 wt % and 10 wt % of the catalyst.
14. The catalyst of any one of paragraphs 1-13, wherein the metal oxide further comprises a second metal selected from the group consisting of rhodium, iridium, and palladium.
15. The catalyst of paragraph 14, wherein the second metal is present in an amount of at least 0.05 wt %, at least 0.1 wt %, at least 0.2 wt %, at least 0.5 wt %, at least 1 wt %, up to 5 wt %, in the range between 0.05 wt % and 5 wt % of the catalyst, between 0.05 wt % and 2 wt % of the catalyst, between 0.05 wt % and 1 wt % of the catalyst, between 0.05 wt % and 0.5 wt % of the catalyst, between 0.1 wt % and 5 wt % of the catalyst, between 0.1 wt % and 2 wt % of the catalyst, between 0.1 wt % and 1 wt % of the catalyst, or between 0.1 wt % and 0.5 wt % of the catalyst.
16. A catalyst comprising
    a silicon dioxide support; and
    a metal oxide, wherein the metal comprises rhenium,
    wherein the rhenium is present in an amount ranging from 0.1 wt % to 10 wt %, and
    wherein at least a portion of the metal oxide is atomically dispersed on the surface of the silicon dioxide support.
17. The catalyst of paragraph 16, wherein the rhenium is present in an amount ranging from 1 wt % to 10 wt %.
18. The catalyst of paragraph 16 or paragraph 17, wherein the metal oxide further comprises rhodium and optionally wherein the rhodium is present in an amount ranging from 0.05 wt % to 5 wt %.
19. The catalyst of any one of paragraphs 16-18, wherein the support comprises a mesoporous material.
20. The catalyst of paragraph 19, wherein the support has an average pore diameter of at least 1 nm, at least 2 nm, at least 3 nm, at least 4 nm, up to 50 nm, up to 40 nm, up to 30 nm, up to 20 nm, up to 10 nm, between 1 nm and 40 nm, between 1 nm and 30 nm, between 1 nm and 20 nm, between 1 nm and 15 nm, or between 1 nm and 10 nm.

21. The catalyst of any one of paragraphs 16-20, wherein the support has a surface area of at least 50 m$^2$/g, at least 100 m$^2$/g, at least 200 m$^2$/g, at least 300 m$^2$/g, at least 400 m$^2$/g, at least 500 m$^2$/g, up to 1000 m$^2$/g, up to 900 m$^2$/g, up to 800 m$^2$/g, between 100 m$^2$/g and 1000 m$^2$/g, between 200 m$^2$/g and 1000 m$^2$/g, between 300 m$^2$/g and 1000 m$^2$/g, between 400 m$^2$/g and 1000 m$^2$/g, or between 500 m$^2$/g and 1000 m$^2$/g.

22. A gas phase plug flow reactor for carbonylation reactions comprising
a reaction chamber;
a catalyst bed inside the reaction chamber, wherein the catalyst of any one of paragraphs 1-21 is packed in the bed;
a gas inlet; and
a gas outlet,
wherein the gas inlet and gas outlet are in fluid communication with the reaction chamber.

23. A method for alcohol carbonylation comprising (i) exposing a mixture of one or more alcohols and carbon monoxide to the catalyst of any one of paragraphs 1-21, wherein the one or more alcohols and carbon monoxide are in the gas phase.

24. The method of paragraph 23, wherein the one or more alcohols are C1-C20 alcohols, C1-C10 alcohols, or C1-C5 alcohols.

25. The method of paragraph 23 or paragraph 24, wherein step (i) is performed at a temperature between 100° C. and 350° C., between 100° C. and 300° C., between 150° C. and 350° C., between 150° C. and 300° C., between 200° C. and 350° C., between 200° C. and 300° C., between 250° C. and 350° C., between 250° C. and 300° C., or between 220° C. and 280° C., and under a pressure of up to 50 bar, up to 45 bar, up to 40 bar, up to 20 bar, up to 10 bar, up to 5 bar, up to 2 bar, up to 1 bar, up to 500 mbar, up to 200 mbar, up to 100 mbar, up to 50 mbar, up to 40 mbar, up to 35 mbar, between 0 and 50 bar, between 0 and 40 bar, between 0 and 20 bar, between 0 and 10 bar, between 0 and 1 bar, between 0 and 100 mbar, between 0 and 50 mbar, between 0 and 40 mbar, or between 0 and 35 mbar.

26. The method of any one of paragraphs 23-25, wherein the one or more alcohols have a single-pass conversion of at least 10%, at least 20%, at least 30%, at least 40%, at least 50%, or at least 60%.

27. The method of any one of paragraphs 23-26, wherein the one or more alcohols are converted to corresponding carboxylic acids at a production rate of at least 0.007 mmol s$^{-1}$ g$_{metal}^{-1}$, at least 0.01 mmol s$^{-1}$ g$_{metal}^{-1}$, at least 0.02 mmol s$^{-1}$ g$_{metal}^{-1}$, or at least 0.03 mmol s$^{-1}$ g$_{metal}^{-1}$.

28. The method of any one of paragraphs 23-27, wherein the one or more alcohols are converted to the corresponding carboxylic acids with a selectivity of at least 60%, at least 65%, at least 70%, at least 75%, at least 80%, at least 85%, at least 90%, or at least 95%.

29. The method of any one of paragraphs 23-28, wherein the catalyst is stable for at least 40 hours, at least 50 hours, or at least 60 hours at a temperature between 100° C. and 350° C., between 200° C. and 350° C., or between 250° C. and 300° C. and a pressure between 0 bar and 50 bar, between 20 bar and 50 bar, or between 20 bar and 40 bar.

30. The method of any one of paragraphs 23-29, further comprising oxidizing the metal oxide with an oxidizing gas prior to step (i).

31. The method of any one of paragraphs 23-30, further comprising recycling a gas stream after step (i).

32. A method for ester carbonylation comprising (i) exposing a mixture of one or more esters and carbon monoxide to the catalyst of any one of paragraphs 1-21, wherein the one or more esters and carbon monoxide are in the gas phase.

33. The method of paragraph 32, wherein the one or more esters are methyl acetate, methyl propionate, methyl butyrate, or a combination thereof.

34. The method of paragraph 32 or paragraph 33, wherein step (i) is performed at a temperature between 100° C. and 350° C., between 200° C. and 350° C., between 220° C. and 300° C., or between 220° C. and 280° C., and under a pressure of up to 1 bar, up to 500 mbar, up to 200 mbar, between 0 bar and 1 bar, between 0 and 500 mbar, between 0 and 400 mbar, between 0 and 300 mbar, or between 0 and 200 mbar.

35. The method of any one of paragraphs 32-34, wherein the one or more esters have a single-pass conversion of at least 0.5%, at least 1%, at least 2%, at least 3%, at least 4%, at least 5%, at least 6%, at least 7%, at least 9%, or from 0.5% to 9%.

36. The method of any one of paragraphs 32-35, wherein the one or more esters are converted to corresponding anhydrides at a production rate of at least 0.0004 mmol s$^{-1}$ g$_{metal}^{-1}$, at least 0.0007 mmol s$^{-1}$ g$_{metal}^{-1}$, at least 0.001 mmol s$^{-1}$ g$_{metal}^{-1}$, at least 0.0015 mmol s$^{-1}$ g$_{metal}^{-1}$, at least 0.002 mmol s$^{-1}$ g$_{metal}^{-1}$, at least 0.0022 mmol s$^{-1}$ g$_{metal}^{-1}$, at least 0.0024 mmol s$^{-1}$ g$_{metal}^{-1}$, at least 0.0026 mmol s$^{-1}$ g$_{metal}^{-1}$, at least 0.0028 mmol s$^{-1}$ g$_{metal}^{-1}$, or from 0.0004 mmol s$^{-1}$ g$_{metal}^{-1}$ to 0.0028 mmol s$^{-1}$ g$_{metal}^{-1}$.

37. The method of any one of paragraphs 32-36, wherein the one or more esters are converted to corresponding anhydrides with a selectivity of at least 10%, at least 12%, at least 15%, at least 17%, at least 18%, at least 19%, at least 20%, at least 21%, at least 22%, from 15% to 25%, from 15% to 22%, or from 17% to 22%.

38. The method of any one of paragraphs 32-37, wherein the catalyst is stable for at least 40 hours, at least 50 hours, or at least 60 hours at a temperature between 100° C. and 350° C., between 200° C. and 350° C., or between 250° C. and 300° C. and a pressure between 0 bar and 50 bar, between 20 bar and 50 bar, or between 20 bar and 40 bar.

39. The method of any one of paragraphs 32-38, further comprising oxidizing the metal oxide with an oxidizing gas prior to step (i).

40. The method of any one of paragraphs 32-39, further comprising recycling a gas stream after step (i).

The present invention will be further understood by reference to the following non-limiting examples.

EXAMPLES

Example 1. Synthesis and Structure Characterization of ReOx/SBA-15 Catalysts

Materials and Methods

ReOx/SBA-15 Catalysts Synthesis

ReOx/SBA-15 catalysts were prepared by introducing water-soluble organics to induce complex formation with metal ions. Triethanolamine (TEA) was chosen, because amino groups can coordinate with metal and the hydroxyl group can coordinate with the support leading to anchoring of the metal to the support surface. Mesoporous SBA-15 with 4 nm pore size (Sigma-Aldrich, 7631-86-9) were used as the support and perrhenic acid solution ($HReO_4$ solution) (Sigma-Aldrich, 75-80 wt % in $H_2O$) were used as the precursor. To synthesize 1% Re in the form of ReOx onto 500 mg SBA-15, 5 mg Re (0.02 mmol) is needed, which corresponds to 0.02 mmol $HReO_4$ (6.75 mg HReO4) precursor. Accordingly, a total of 8.4 mg $HReO_4$ solution was used. The amount of $HReO_4$ solution needed to prepare 5%, 10%, or 20% Re weight loading in the ReOx/SBA-15 catalyst was calculated following the above calculation.

The support was chosen based on its high surface area and inertness. For the deposition of $ReO_x$ species, appropriate amounts of Re precursor were dissolved in 10 mL of high-performance liquid chromatography (HPLC) grade water (JT4218-3, J. T. Baker) and the desired amounts of TEA with 8 times molar of Re was added into the solution under magnetic stirring for 30 min. The addition of 8:1 molar ratio of TEA is to promote Re dispersion. The Re precursor solution was mixed with the 100 mL SBA-15 support suspension under magnetic stirring with syringe pump under 5 mL/hr injection speed. After mixing for 12 hours at room temperature, the solution was dried at 80° C. by rotary evaporator. Before the catalyst characterization and reactivity, the sample was calcined at 450° C. for 4 hours under dry air.

ReOx/SBA-15 Catalysts Characterization
Ultraviolet-Visible Diffuse Reflectance Spectroscopy UV-Vis diffuse reflectance spectra were used to characterize the structure of $ReO_x$ on SBA-15. The spectrums were obtained using dehydrated MgO as a reference with a Thermo Scientific Evolution 300 UV-Vis spectrometer equipped with a Harrick Scientific Praying Mantis diffuse reflectance accessory. Samples were lightly ground using a mortar and a pestle and dehydrated at 350° C. for 1 hour in flowing dry air and reaction conditions (30 mbar methanol and 30 mbar CO at 250° C.). Calculation of the onset of photon absorption induced by ligand to metal charge transfer (LMCT) was described previously (Lwin, et al., ACS Catal., 2015, 5 (3), 1432-1444; Barton, et al., J. Phys. Chem. B, 1999, 103, 630-640). For comparison, the LMCT onsets for $KReO_4$ and $Re_2O_7$ were obtained, representing isolated $ReO_4$ and bulk ReOx species, respectively. The bandgap energy (Eg) of reference compounds representing isolated and oligomeric $Re_xO_y$, such as $KReO_4$ and $Re_2O_7$, were collected for comparison.

High-Angle Annular Dark Field-Scanning Transmission Electron Microscopy (HAADF-STEM)

Besides UV-Vis, 10-20 scanning transmission electron microscopy (STEM) images on each sample after calcination at 450° C. for 4 hour was also collected. Atomic resolution high-angle annular dark field scanning transmission electron microscopy (HAADF-STEM) imaging was performed on a JEOL Grand ARM300CF microscope with double aberration correctors at 300 kV. Images were collected after ex-situ calcination of samples at 450° C. using a convergence semiangle of 22 mrad, and inner- and outer-collection angles of 83 and 165 mrad, respectively. A beam current of 11 pA was used with pixel time of 4 μs.

X-Ray Absorption Spectroscopy (XAS)

XAS at the Re L3 edge (10535 eV) was executed on beamlines 4-1 and 9-3 at the Stanford Synchrotron Radiation Lightsource at the SLAC National Laboratory using a Si(220) double crystal monochromator. Spectra of Re reference compounds were collected by pressing finely ground powders into self-supporting pellets, while Re metal powder was smeared as a thin film on Kapton tape. In a typical experiment, 30 mg of catalyst was crushed, sieved (80-120 mesh), and loaded into a 1 cm catalyst bed in a 3 mm quartz tube flow-through reactor held perpendicular to the X-ray source (Hoffman, et al., J. Synchrotron Radiat. 2018, 25 (6), 1673-1682). Samples were diluted with mesoporous silica (MCM-41) to have an absorption length of 2.0 with a fractional absorbance of Re of about 0.2. A W foil was scanned simultaneously for energy calibration. In-situ extended X-ray absorption fine structure (EXAFS) measurements, consisting of 9-16 scans, were collected at 50° C. following exposure to oxidizing (20% $O_2$/He, 350° C., 1 h) or reaction conditions (150 mbar methanol and 200 mbar CO in He, 250° C., 1 h).

The raw data were processed using the Athena interface of Demeter software package (Ravel, et al., J. Synchrotron Radiat., 2005, 12 (4), 537-541). Spectra were energy calibrated, merged, and normalized. The EXAFS were extracted in k-space and Fourier transformed using the $k^2$-weighted EXAFS function (k=3.9-14) to amplify oscillations at high k-values. EXAFS fitting was carried out over the R range (1-2.2 Å) taking into account $k^1$-, $k^2$-, and $k^3$-weighting using the Artemis interface of Demeter. Phase shifts and amplitude for relevant backscattering paths were calculated using FEFF6 (Rehr, et al., Phys. Rev. Lett., 1992, 69 (23), 3397-3400). $S_o^2$ was determined to be 0.73±0.04 by fitting the Re metal standard (data not shown). A multiple data set fit was performed for the 5, 10, and 20 wt % Re loading samples simultaneously to minimize errors. Spectra were fit with two Re—O scattering paths derived from the crystal structure of tetrahedral Re in $Re_2O_7$ (mp-1016092). Coordination numbers to the short (double bonded) Re═O scattering path and long (single bonded) Re—O scattering path were fixed at 3 and 1, respectively, consistent with previous EXAFS treatment of similar samples, and the +7 Re oxidation state was inferred from X-ray absorption near edge structure (XANES) measurements (Vicente, et al., J. Phys. Chem. C, 2011, 115 (18), 9012-9024; Bare, et al., J. Phys. Chem. C, 2011, 115 (13), 5740-5755).

Temperature-Programmed Desorption of Ammonia ($NH_3$-TPD)

$NH_3$-TPD measurements were performed on a Micromeritics AutoChem 2920 instrument. In a typical experiment, 0.15 g of catalyst was loaded into a U-shaped, flow-thru, quartz sample tube. Prior to measurements, the catalyst was pretreated in $O_2$ (30 $cm^3$/min) at 350° C. for 1 h to remove adsorbed water. A mixture of 10% $NH_3$/90% helium was flown over the catalyst (30 $cm^3$/min) at 50° C. for 1 h. Then the sample was flushed with pure helium (30 $cm^3$/min) at 50° C. for 1 h. The TPD measurements were carried out in the range 100-350° C. at a heating rate of 10° C./min $NH_3$ concentration in the effluent was monitored with a gold-plated filament thermal conductivity detector. The amount of desorbed NH3 was determined based on the calibrated area under the desorption curve.

X-Ray Photoelectron Spectroscopy (XPS)

High-resolution XPS measurements were performed on an Escalab Xi+(Thermo-Fisher) XPS microprobe equipped with a monochromatic Al anode Xray source. The pressure in the XPS chamber was maintained below $1\times10^{-9}$ Torr during the acquisition process. XPS measurements were performed using the vacuum/inert transfer vessel with the use of glovebox for the sample preparation and transfer to enable analysis after pretreatment without exposure to atmosphere.

Fourier Transform Infrared Spectroscopy (FTIR)

Catalysts were loaded into a Harrick Praying Mantis reaction chamber with ZnSe windows mounted inside a Thermo Scientific Praying Mantis diffuse reflectance adapter set inside a Thermo Scientific Nicolet iS10 Fourier transform infrared spectroscopy (FTIR) spectrometer. All gases were passed across an isopropyl alcohol/liquid nitrogen cold trap and a glass trap filled with Drierite desiccant to remove trace moisture. Before characterization, catalysts were pretreated via in situ oxidation at 350° C. for 1 h under $O_2$ flow, and a background spectrum was taken before CO and methanol introduction. The CO partial pressure was kept as 30 mbar, and methanol partial pressures were chosen as 42, 105, and 150 mbar with helium as a carrier gas. The spectra were collected under methanol and CO. In all measurements, spectra were obtained by averaging 32 sequentially collected scans at a resolution of 4 $cm^{-1}$.

Results

Figure 1:
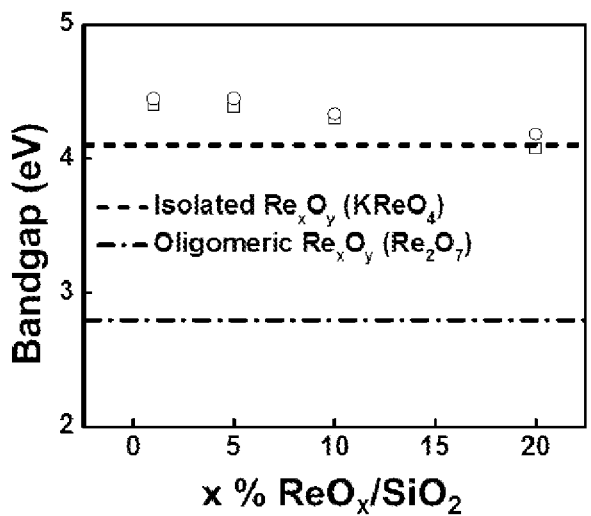
FIG. 1 is a graph showing bandgap energies of dehydrated $ReO_x$/SBA-15 catalysts (also referred herein as "Re—$SiO_2$"

To provide sample-averaged information on the ReOx structure without influence of the elctron beam, UV-vis and XAS were performed. In-situ UV-vis spectroscopy measurements of the edge energy (Eg) for the LMCT electronic transition were executed under an oxidative environment, and reaction conditions. Eg provides useful information regarding the electronic structure of the ReOx species, which is sensitive to the ReOx domain size and structure (moving from discrete electronic structure of monomeric species to bands existing in bulk structures). The Eg of $ReO_x$/SBA-15 catalysts after dehydration was measured with in situ UV-Vis spectroscopy to determine the domain size of $ReO_x$ species, as shown in FIG. 1. The Eg reflects the electronic structure determined by local environments such as the level of distortion, number of nearest polyhedral neighbors, and bonds between each of those neighbors (Barton, D. G., et al., *J. Phys. Chem. B*, 103(4):630-640 (1999) Lwin, S. et al., *ACS Catal.*, 5:1432-1444 (2015)). As seen in FIG. 1, the bandgap energies of $KReO_4$ and $Re_2O_7$, representing isolated and oligomeric Re oxide species, were 4.1 and 2.8 eV, respectively, demonstrating that the bandgap energy depends on the $ReO_x$ domain size.

The samples were treated under two conditions: oxidation at 350° C. for 1 h (circles in FIG. 1) and oxidation at 350° C. for 1 h and then reduction at 250° C. for 1 h which is similar with reaction conditions (squares in FIG. 1). The reaction was at 250° C. Under both conditions, the Ep shows a similar trends. The bandgap energy of $ReO_x$/SBA-15 with Re weight loading of 1% and 5% was 4.45 eV, demonstrating that under these weight loadings, $ReO_x$ resided as isolated species on SBA-15. When the Re weight loading of the $ReO_x$/SBA-15 catalyst is 10%, the sample showed a lower bandgap energy at 4.3 eV, which demonstrates that $ReO_x$ is mainly isolated dispersed, but there is some Re cluster formation. The bandgap energy of $ReO_x$/SBA-15 where the Re weight loading is 20% was below 4.1 eV, demonstrating that at this weight loading, $ReO_x$ structure is mainly in a cluster. A comparison of the Eg values to those of control samples, dispersed ($KReO_4$, Eg=4.1 eV) species, and bulk ($Re_2O_7$, Eg=2.8 eV) ReOx species, shows that at lower Re weight loadings (1, 5, and 10 wt %), ReOx exists predominantly in the form of atomically dispersed species, while ReOx clusters are present at higher Re weight loadings and their size increases with increasing Re loading. The similar Eg following calcination and reaction conditions shows that ReOx domains remain stable under reaction conditions. This is in contrast to a previous report in which ReOx on $SiO_2$ was unstable after 2 h during 2-butanol dehydration (She, et al., *ACS Catal.*, 2012, 2 (6), 1020-1026), demonstrating that the use of TEA during synthesis promotes the stability of a highly dispersed ReOx species on $SiO_2$.

The $ReO_x$ structures at different weight loading are also supported by HAADF-STEM images of the calcined (450° C., dry air) samples. In HAADF-STEM, the higher atomic number of Re as compared to Si allows identification of Re domains via increased scattering of the electron beam. While atomically dispersed ReOx species were primarily observed for the 5 wt % Re sample, an increase in the density and existence of ReOx clusters was observed with increasing Re loading to 10 and 20 wt %. The fraction of ReOx clusters in each sample is likely an over estimation of the as-prepared state due to the electron beam induced coalescense during image acquisition (Mishra, et al., *MRS Bull.*, 2017, 42 (9), 644-652). Previous analysis of WOx species on ZrOx noted that analysis by STEM imaging showed higher concentrations of WOx clusters than atomically dispersed species as compared to correlated spectrscopic measurements (Zhou, et al., *Nat. Chem.*, 2009, 1 (9), 722-728). Accordingly, the STEM results show that $ReO_x$ of 5% Re weight loading was isolated dispersed on SBA-15 (data not shown). For the $ReO_x$/SBA-15 catalyst where the Re weight loading is 10%, some $ReO_x$ clusters form, and for the $ReO_x$/SBA-15 catalyst where the Re weight loading is 20%, mainly $ReO_x$ clusters were present.

XAS was used to further characterize the oxidation state and structure of ReOx species on the support. ReOx/SBA-15 samples of various Re weight loadings showed nearly identical XANES spectra following oxidation (data not shown), with edge energies correlating to Re in +7 oxidation state, which was also confirmed by XPS (data not shown). EXAFS spectra were fit with a proposed $ReO_4$ model that is consistent with the Re +7 oxidation state observed from XANES, in which Re makes a single bond to the support via oxygen (Re—O 1.77±0.04 Å), and is coordinated to three additional Re=O double bonds (Re—O 1.69±0.01 Å). The fit yielded a good match to the measured EXAFS spectrum for the 5 wt % Re sample (see FIG. 9). The EXAFS data and fit (data not shown) are also in agreement with previously reported structures of atomically dispersed $ReO_4$ (Vicente, et al., *J. Phys. Chem. C*, 2011, 115 (18), 9012-9024; Bare, et al., *J. Phys. Chem. C*, 2011, 115 (13), 5740-5755). Notably, the EXAFS data for the 5, 10, and 20 wt % Re samples did not vary considerably (data not shown), showing that this sample averaged technique may not be able to unambiguously identify small, subnanometer ReOx clusters within a sample containing atomically dispersed $ReO_4$ species (Resasco, et al., *J. Am. Chem. Soc.*, 2020, 142 (1), 169-184). This is not unsuspected, as even bulk crystalline oligomeric Re species ($Re_2O_7$) show Re—O—Re scattering at long bond lengths (data not shown), which is thus more sensitive to destructive interference from competing multiple scattering paths. Therefore, EXAFS likely, in contrast to STEM, underestimates the existence of ReOx clusters present.

On the basis of a combination of STEM, UV-vis and XAS, it was concluded that ReOx was primarily atomically dispersed as $ReO_4$ species for 1 and 5 wt % Re, a mix of atomically dispersed $ReO_4$ and small ReOx clusters for 10 wt % Re, and primarily in the form of ReOx clusters for 20 wt % Re.

Example 2. The ReOx/SBA-15 Catalysts Catalyze Methanol Carbonylation to Acetic Acid at a High Production Rate and Selectivity Materials and Methods The catalytic activity for methanol carbonylation was evaluated in a fixed-bed quartz reactor in the temperature range of 220-280° C. operating at atmospheric pressure. All gas flows were controlled by mass flow controllers (Teledyne Hastings) and an in-line bubbler was used to deliver gas phase methanol (Fisher Scientific, HPLC Grade, LOT: 177964) to the catalyst. Helium (Airgas, UHP, 99.999%) was used to bubble methanol and used as a diluent to control the methanol partial pressure. The reaction effluent was quantified with online mass spectrometry (HALO 201, Hiden Analytical Inc.). The following m/z values were used to detect each product: m/z=28 for CO, m/z=31 for MeOH, m/z=45 for dimethyl ether, m/z=60 for acetic acid, and m/z=74 for methyl acetate. The concentrations were calibrated to the signal intensity at each mass and Helium was used as an internal standard. The mass spec results were compared to calibrated analysis via gas chromatography, which showed quantitative agreement and the ability to close mass balances within ~5% under all explored conditions.

Prior to reactivity measurements, catalysts were treated by oxidation at 350° C. for 1 hour with pure $O_2$ at 50 mL min$^{-1}$, followed by measurements at varying temperatures. The system was maintained for two hours at each temperature to ensure steady state was achieved.

Different ReOx/SBA-15 catalysts were tested with 1, 5, 10, and 20 wt % Re weight loading. During kinetic measurements, the total Re weight loading in the reactor was kept constant by using different weights of catalysts and diluent SBA-15. Additionally, $SiO_2$ gel was added to minimize the pressure drop (Table 2). For the measurement of different Re weight loading, 100 mg 1% ReO$_x$/SBA-15 catalyst was diluted in 400 mg $SiO_2$; 20 mg 5% ReO$_x$/SBA-15 was diluted in 400 mg balanced with 80 mg SBA-15; 10 mg 10% ReO$_x$/SBA-15 was diluted in 400 mg $SiO_2$ with 90 mg SBA-15; 5 mg 20% ReO$_x$/SBA-15 was diluted in 400 mg $SiO_2$ with 95 mg SBA-15. The percentage (i.e. 1%, 5%, 10% or 20%) refers to the weight loading of Re in each ReOx/SBA-15 catalyst (weight of Re relative to the weight of the catalyst). For example, 1% ReOx/SBA-15 catalyst (also referred herein as "1 wt % ReOx/SBA-15") refers to a ReOx/SBA-15 catalyst where 1 wt % Re is present in the ReOx/SBA-15 catalyst. The ReOx/SBA-15 catalysts are also referred to herein as "Re—$SiO_2$" or "Re/$SiO_2$".

TABLE 2

The amount of catalysts used for methanol carbonylation reactivity measurement with different Re weight loadings.

| Re weight loading | Catalyst weight (mg) | Balanced SBA-15 (mg) | $SiO_2$ as dilution (mg) |
|---|---|---|---|
| 1 wt. % ReOx/SBA-15 | 100 | 0 | 400 |
| 5 wt. % ReOx/SBA-15 | 20 | 80 | 400 |
| 10 wt. % ReOx/SBA-15 | 10 | 90 | 400 |
| 20 wt. % ReOx/SBA-15 | 5 | 95 | 400 |
| $Re_2O_7$ mixed with $SiO_2$ | 1 | 99 | 400 |

When analyzing the influence of methanol conversion on selectivity over the 10 wt % ReOx/SBA-15 catalyst, the amounts of both Re and SBA-15 were varied, while the amount of diluent $SiO_2$ was kept constant (Table 3). For different weights of 10% ReO$_x$/SBA-15 measurement, 30 mg 10% ReO$_x$/SBA-15 catalyst was diluted in 600 mg $SiO_2$ balanced with 270 mg SBA-15; 60 mg 10% ReO$_x$/SBA-15 was diluted in 600 mg $SiO_2$ with 240 mg SBA-15; 90 mg 10% ReO$_x$/SBA-15 was diluted in 600 mg $SiO_2$ with 210 mg SBA-15; 180 mg 10% ReO$_x$/SBA-15 was diluted in 600 mg $SiO_2$ with 120 mg SBA-15; 300 mg 10% ReO$_x$/SBA-15 was diluted in 600 mg $SiO_2$; 600 mg 10% ReO$_x$/SBA-15 was diluted in 600 mg $SiO_2$. Again, the percentage (i.e. 10%) refers to the weight loading of Re in each ReOx/SBA-15 catalyst (weight of Re relative to the weight of the catalyst). For example, 10% ReO$_x$/SBA-15 (also referred herein as 10 wt % ReOx/SBA-15) catalyst refers to a ReOx/SBA-15 catalyst where 10 wt % Re is present in the ReOx/SBA-15 catalyst.

TABLE 3

The amount of catalysts used to promote methanol conversion during methanol carbonylation reaction with 10 wt. % ReOx/SBA-15.

| Catalysts weight (mg) | Balanced SBA-15 (mg) | $SiO_2$ as dilution |
|---|---|---|
| 30 | 270 | 600 |
| 60 | 240 | 600 |
| 90 | 210 | 600 |
| 180 | 120 | 600 |
| 300 | 300 | 600 |
| 600 | 0 | 600 |

The stability measurement was performed with 600 mg 10% ReO$_x$/SBA-15 diluted in 600 mg $SiO_2$ at 280° C.

Results

Based on the UV-vis, STEM, and XAS results described above, the structure of ReO$_x$ on 1%, 5% and 10% Re weight loading on ReO$_x$/SBA-15 catalysts are mainly isolated species whereas 20% Re weight loading on ReO$_x$/SBA-15 catalysts are mainly clustered. As noted above, ReOx/SBA-15 catalysts having 1%, 5%, 10%, or 20% Re weight loadings are also referred herein as 1% ReOx/SBA-15 (or "1 wt % ReOx/SBA-15), 5% ReOx/SBA-15 (or "5 wt % ReOx/SBA-15), 10% ReOx/SBA-15 (or "10 wt % ReOx/SBA-15), or 20% ReOx/SBA-15 (or "20 wt % ReOx/SBA-15), respectively.

The influence of ReO$_x$ structure on methanol carbonylation reactivity and selectivity was examined on these samples by comparing reactivity as a function of Re weight loading. Bulk $Re_2O_7$ was also used to calibrate the reactivity of extended ReOx domains. Catalysts were pre-oxidized at 350° C. in $O_2$ and then exposed to a gas mixture of methanol and CO at a molar ratio of 1:1 for reactivity measurements (at 30 mbar of each) with a balance of helium at atmospheric pressure. The reaction was executed in the kinetically limited regime by keeping the methanol conversion below 10%. AA production rate for 10 wt % ReOx/SBA-15 measured at 280° C. and 30 mbar methanol and CO (balance He) was plotted as a function of the square root of the superficial velocity (data not shown). The production rates were observed to be independent of the superficial velocity showing a lack of mass transfer limitations. A superficial velocity of 100 cm$^3$ min$^{-1}$ (20 cm$^3$ min$^{-1}$ of He to purge methanol and 30 cm$^3$ min$^{-1}$ of 10% CO/He with 50 cm$^3$ min$^{-1}$ of He) was chosen for all kinetic experiments.

In the temperature range of 220 to 280° C., the detectable products are acetic acid (AA), dimethyl ether (DME), methyl acetate (MA) and formaldehyde. ReO$_x$ will promote acidity of SBA-15 support (Liu, S., et al., *ChemSusChem*, 11:1446-1454 (2018)), so methanol could dehydrate into methoxy group on the acidic ReO$_x$ sites (Jehng, J.-M., et al., *Catal. Today*, 28:335-350 (1996)).

The mechanism for AA formation during methanol carbonylation is that gas phase CO attacks a surface methoxy group at ReO$_x$ acidic sites and produces AA with ReO$_x$ sites restoring (Boronat, M., et al., *Phys. Chem. Chem. Phys.*, 13:2603-2612 (2011)). Two possible reaction pathways for DME formation are gas phase methanol reaction with surface methoxy groups, i.e. the dissociative mechanism (Corma, A., et al., *J. Am. Chem. Soc.*, 130:16316-16323 (2008)), and the combination of two surface methoxy groups that produce DME, i.e. the associative mechanism (Akarmazyan, S. S., et al., *Appl. Catal. B Environ.*, 145:136-148 (2014); Qi, J. & Christopher, P., *Ind. Eng. Chem. Res.*, 58:12632-12641 (2019)). DME can further react with surface acetyl moiety which is produced after CO insert onto surface methoxy to yield MA (Blasco, T. et al., *Angew. Chemie-Int. Ed.*, 46:3938-3941 (2007); Cheung, P., et al., *Angew. Chemie-Int. Ed.*, 45:1617-1620 (2006)). Formaldehyde formed from methoxy group dehydration (Tsoncheva, T., et al., *J. Mol. Catal. A Chem.*, 225:245-251 (2005); Tsoncheva, T., et al., *Can. J. Chem.*, 85:118-123 (2007)) was also detected.

The production rates of AA and DME as a function of Re weight loading are shown in FIGS. 2A-2B. All the production rates are based on the weight of Re. The results for MA and formaldehyde production rates are shown in FIGS. 10A-10B. The bare SBA-15 support showed no measurable reactivity under these conditions. The methanol conversions in these measurements were kept below 5%. Both the 1% and 5% ReO$_x$/SBA-15 catalysts present similar AA and DME production rates over the entire explored temperature range from 220 to 280° C. The AA production rate increases from 0.0001 to 0.038 mmol s$^{-1}$ g$_{Re}^{-1}$ and DME production rate increases from 0.000065 to 0.0005 mmol s$^{-1}$ g$_{Re}^{-1}$ with the increase of temperature from 220 to 280° C. (see FIGS. 2A-2B). For 1 and 5 wt % ReOx/SBA-15 catalysts, the AA and DME production rates were indistinguishable, showing 0.038 and 0.0005 mmol s$^{-1}$ g$_{Re}^{-1}$, respectively, at 280° C.

As discussed above, the UV-vis and STEM results show that under these two weight loadings, ReO$_x$ structure on the SBA-15 support is isolated. Therefore, the methoxy groups formed from methanol dehydration on ReO$_x$ are also isolated, which inhibits DME formation. The only pathway for DME formation is through surface methoxy groups reacting with gas phase methanol. AA is formed from gas phase CO reacting with surface methoxy groups.

For the ReOx/SBA-15 catalysts containing 10% Re weight loading on SBA-15, the AA production rate decreased to 0.0285 mmol s$^{-1}$ g$_{Re}^{-1}$ at 280° C. and the DME production increased to 0.0006 mmol s$^{-1}$ g$_{Re}^{-1}$. The UV-vis analysis and STEM results demonstrate that the dominant structure of ReO$_x$ on 10% ReOx/SBA-15 catalysts is isolated dispersed, with some clustering. The increase of DME production rate demonstrates that when ReO$_x$ clusters exist, DME is formed not only from gas phase methanol reacting with surface methoxy, but also from combination of two surface methoxy groups.

When the Re weight loading goes up to 20%, ReO$_x$ is primarily in the form of clusters on the SBA-15 support. The results show that under 20% weight loading, DME becomes the major product (see FIGS. 2A-2B). In the entire temperature range, the production rate of DME increases from 0.00002 to 0.02 mmol s$^{-1}$ g$_{Re}^{-1}$, which is more than 30 times higher than those under 1%, 5%, and 10% Re weight loadings. In addition, the AA production rate decreases to 0.007 mmol s$^{-1}$ g$_{Re}^{-1}$ at 280° C. These results show that the primary reaction pathway on ReO$_x$ clusters is DME formation, and the mechanism for the DME formation includes both gas phase methanol attacking surface methoxy groups and combination of two surface methoxy groups. Also, the combination of two surface methoxy groups pathway shows lower energy barrier than gas phase attacking surface methoxy groups pathway. Therefore, increasing the Re loading to 20 wt % resulted in a 30-fold increase in the DME production rate at 280° C., while the AA production rate decreased by 5-fold compared to that of the 1 and 5 wt % ReOx/SBA-15. Compared to the 20 wt % Re sample at 280° C., bulk Re$_2$O$_7$ showed a DME production rate of only 2-fold higher and a 50% lower AA production rate. The similar reactivity of 20 wt % ReOx/SBA-15 and Re$_2$O$_7$, and their stark difference to the behavior of samples with 10 wt % Re or less, substantiate the use of Re weight loading variation for comparing the behavior of atomically dispersed ReO$_4$ and ReOx clusters.

The measured apparent activation energies (Eapp) for AA and DME formation were similar for 1 and 5 wt % ReOx/SBA-15, showing Eapp of ~130±30 kJ/mol and ~100±40 kJ/mol for AA and DME formation, respectively. On 10 wt % ReOx/SBA-15, the Eapp for AA and DME formation were 155±20 and 112±28 kJ/mol, respectively. The slight deviation of the Eapp on 10 wt % ReOx/SBA-15 from 1 and 5 wt % ReOx/SBA-15, demonstrates relatively consistent active site distributions with a small increase in ReOx cluster formation at the higher weight loading, in agreement with inferences from catalyst characterization. On the 20 wt % ReOx/SBA-15, the Eapp for AA and DME were much higher, 259±64 and 257±9 kJ/mol, respectively. Bulk Re$_2$O$_7$ exhibited Eapp of 272±33 and 273±32 kJ/mol for the formation of AA and DME, respectively, which are statistically similar to the 20 wt % ReOx/SBA-15 sample. There is some apparent deviation from Arrhenius like behavior at lower temperatures. This likely arises from the low analytical signals at these temperatures rather than a true deviation from exponential behavior.

Differences in the measured Eapp for AA and DME formation over atomically dispersed ReO$_4$ versus ReOx clusters on SiO$_2$ and bulk Re$_2$O$_7$ are derived from differences in acidity, as measured by NH$_3$ temperature-programmed desorption shown in FIG. 11 structure. This demonstrates that ReOx domain size dictates acid strength. The product formation rates and Eapp on the 1, 5, and 10 wt % ReOx/SBA-15 catalysts provide evidence that a consistent active site exists with a close to linear relationship between site density and reactivity. The reactivity results here show that either the majority of sites on ReOx/SBA-15 are active, or the same fraction of active sites are produced for different weight loadings (Chauvin, et al., *J. Chem. Soc., Chem. Commun.*, 1992, 6, 462-464).

FIG. 3 shows the measured selectivity for AA production in the range of 220-280° C., where samples at lower weight loadings (1%, 5% and 10 wt % ReOx/SBA-15) exhibit an AA selectivity of ~93% at >250° C., whereas 20 wt % ReOx/SBA-15 and bulk Re$_2$O$_7$ exhibited AA selectivity <20% across all temperatures. Note that at above 280° C., a significant increase in the rates of byproduct formation were observed, resulting in a decrease in AA selectivity.

On the basis of the characterization and methanol carbonylation reactivity results, it is concluded that atomically dispersed ReO$_4$ species on SiO$_2$ are selective for AA formation, whereas ReOx clusters and bulk Re$_2$O$_7$ with stronger acid sites primarily drive DME production. This demonstrates that communicating acidic sites that exist on the surface of ReOx clusters facilitate the rate of methanol coupling to DME.

The DME carbonylation reaction was tested on 5 wt % ReOx/SBA-15 using 30 mbar DME and 30 mbar CO in the feed (see FIG. 12). The DME carbonylation reaction to MA proceeded at a rate 12 times higher than that of methanol carbonylation to AA under identical conditions. This highlights the role of minimizing DME formation pathways for obtaining high selectivity to AA. Water, which is a product during DME formation, may compete with other reaction intermediates at Lewis acid sites and may poison active sites that contribute to the production of AA (Corma, et al., *J. Am. Chem. Soc.*, 2008, 130 (48), 16316-16323; Cheung, et al., *Angew. Chem., Int. Ed.*, 2006, 45 (10), 1617-1620).

Example 3. The ReOx/SBA-15 Catalysts Catalyze Methanol Carbonylation to Acetic Acid with High Single Pass Conversion Materials and Methods Catalysts were pre-oxidized at 350° C. in $O_2$ and then exposed to a gas mixture of methanol and CO at a molar ratio of 1:1 for reactivity measurements (33 mbar methanol and 33 mbar CO with balance inert).

Results

The influence of methanol conversion on AA selectivity and catalyst stability for the 10 wt % ReOx/SBA-15 catalyst was investigated, which exhibited the highest volumetric AA production rates still with good selectivity (see FIG. 4). To analyze the influence of methanol conversion on selectivity, the 10 wt % ReOx/SBA-15 in the reactor was increased, while the amount of diluent SBA-15 was decreased such that the space velocity was identical in all experiments. Increasing the catalyst loading resulted in increasing methanol conversion to ~60%, which was limited from further increases based on the reactor size. The measured AA selectivity was independent of methanol conversion, showing ~93% selectivity for different methanol conversions (FIG. 5). The highest conversion achieved with 600 mg material is around 60% (see FIG. 4) and the selectivity to AA is still as high as 93% (see FIG. 5), which shows that the conversion can be significantly increased to meet industrial standards using this ReOx/SBA-15 catalyst.

Example 4. The ReOx/SBA-15 Catalysts Catalyze Methanol Carbonylation to Acetic Acid with High Stability Materials and Methods The stability test was performed on 600 mg of 10% $ReO_x$/SBA-15 catalysts, diluted in 600 mg $SiO_2$. This weight loading was chosen as it exhibited the highest selectivity with the highest ReOx weight loading showing isolated structures. The stability of 10% $ReO_x$/SBA-15 catalysts was examined at 280° C. in a stoichiometric feed of methanol and CO (i.e. 30 mbar) with pressure of 30 mbar.

Results

No measurable change in both reactivity and selectivity of the 10% $ReO_x$/SBA-15 catalysts was observed during the 60 hours measurement period (see FIG. 6). FIG. 6 shows a stable ~60% methanol conversion and 93% AA selectivity over 60 h on stream, demonstrating that the atomically dispersed $ReO_4$ active sites (i.e. the active sites associated with AA formation) on $SiO_2$ remain quite stable under the explored reaction conditions (i.e. e.g. 280° C. and pressure of 30 mbar).

Example 5. Reaction Pathway for Methanol Carbonylation to AA on $ReO_4$/$SiO_2$

Materials and Methods

Mechanistic insights into the observed AA formation on atomically dispersed $ReO_4$ species and ReOx clusters were developed by executing methanol carbonylation on 10 and 20 wt % ReOx/SBA-15 at 280° C. with independently varied methanol and CO partial pressures in the range of 30 to 330 mbar and 200 to 600 mbar, respectively.

For methanol and CO pressure-dependent experiments, 10 wt % ReOx/SBA-15 was pretreated by oxidation at 350° C. for 1 h. After the pretreatment, while maintaining a constant temperature of 280° C. and methanol partial pressure at 30 mbar, the CO partial pressure was varied from 200 mbar to 600 mbar with Ar as a diluent. Alternatively, while maintaining a constant temperature of 280° C. and CO partial pressure at 30 mbar, the methanol partial pressure was varied from 30 mbar to 330 mbar and Ar acted as a diluent. The reaction system was held at each condition for 2 h to ensure steady state conditions.

Results

FIG. 13A shows that for 10 wt % ReOx/SBA-15 (mostly atomically dispersed $ReO_4$), a first-order dependence of AA production on methanol partial pressure was observed in the range of 30-90 mbar, which transitioned to a zero-order dependence at higher methanol pressure. This shows that methanol, or a methanol derived intermediate, is first-order in the rate-determining step (RDS) and saturates the active site at methanol partial pressures >~120 mbar. For 20 wt % ReOx/SBA-15 that contained a mix of atomically dispersed $ReO_4$ and ReOx clusters, a ~0.6 reaction order for methanol partial pressure in the AA production rate was observed from 30 to 85 mbar, with an apparent decrease in methanol reaction order at ~85 mbar, followed by a small increase in methanol reaction order up to ~120 mbar, and finally a reaction order of 0 above ~120 mbar. The distinct kinetic behavior of the two types of sites is consistent with the differences in Eapp for AA formation observed in FIGS. 2A-2B and 3 may also be influenced by $H_2O$ produced due to DME formation.

In contrast to methanol, the AA production rate exhibited nearly a first-order (0.8-0.9) dependence on CO partial pressure for both catalysts across a broad partial pressure range from 200 to 600 mbar CO (see FIG. 13B). This shows that CO is involved in the RDS and that CO does not exist as an adsorbed species at an appreciable coverage on the active site (Bhan, et al., *J. Am. Chem. Soc.*, 2007, 129 (16), 4919-4924; Cheung, et al., *Angew. Chem., Int. Ed.*, 2006, 45 (10), 1617-1620; Cheung, et al., *J. Catal.*, 2007, 245 (1), 110-123).

The nature of bound species during AA formation on atomically dispersed $ReO_4$ species was analyzed via in situ FTIR measurements executed under varying methanol partial pressure (at a constant CO partial pressure of 30 mbar) at 280° C. on 5 wt % ReOx/SBA-15 (data not shown). Independent of the methanol partial pressures, two strong bands at 2954 and 2854 $cm^{-1}$ were observed that correspond to physiosorbed methanol on $SiO_2$, as they were also seen on pure $SiO_2$ (see FIG. 14) (Liu, et al., *Catal. Lett.*, 2008, 120 (3-4), 274-280; Clarke, et al., *J. Catal.*, 1994, 150, 81-93). Three bands at 2979, 2922, and 2822 $cm^{-1}$ (marked with the dashed lines) were also observed. The 2979 and 2922 $cm^{-1}$ bands are assigned to the asymmetric and symmetric stretches of $CH_3$ in —$OCH_3$ bound to $ReO_4$, respectively, while 2822 $cm^{-1}$ is assigned as the first overtone of the symmetric stretch (Burcham, et al., *Langmuir*, 2001, 17 (20), 6164-6174).

Alcohol activation on the homogeneous methyltrioxorhenium complex (MTO, $CH_3ReO_3$), in which Re exists in a +7 oxidation state, has been studied previously (Zhu, et al., *J. Org. Chem.*, 1996, 61 (1), 324-328; Jacob, et al., *Organometallics*, 1998, 17 (9), 1835-1840; Korstanje, et al., *Chem.-Eur. J.*, 2013, 19 (39), 13224-13234). On the basis of theoretical analysis and isotopic labeling experiments, it was proposed that dissociative alcohol adsorption occurs through proton transfer from the alcohol to an oxygen native of MTO, resulting in the coordination of —OR group to the Lewis acidic Re center, thus maintaining a +7 oxidation state of Re. This is analogous to the mechanism for ethanol activation over Lewis acidic $Al_2O_3$ surfaces, where —$OCH_2CH_3$ coordinates to the Lewis acidic Al center, while the proton transfers to a neighboring oxygen (Christiansen, et al., *ACS Catal.*, 2013, 3(9), 1965-1975; DeWilde, et al., *ACS Catal.*, 2013, 3(4), 798-807; Roy, et al., *ACS Catal.*, 2012, 2 (9), 1846-1853; Christiansen, et al., *J. Catal.*, 2015, 323, 121-131; Secordel, et al., *Catal. Today*, 2010, 155, 177-183). Thus, methanol adsorption onto $ReO_4$ occurs dissociatively at the O—H group, resulting in the formation of Re(—O—Si)(—OH)(=O)$_2$(—$OCH_3$), where Re remains in a +7 oxidation state.

With increasing methanol partial pressure in the feed from 42 to 105 mbar, an increase in the intensity of the bands assigned to —$OCH_3$ stretches was observed, showing an increase in the coverage on $ReO_4$ sites. However, the —$OCH_3$ stretch intensities remained unchanged with further increase in the methanol partial pressure to 150 mbar, demonstrating saturation of adsorption sites on $ReO_4$ species. The in situ FTIR results are consistent with the kinetic measurements shown in FIG. 13A, where a saturation in the methanol reaction order in AA formation rate correlates with a saturation in —$OCH_3$ adsorption sites. This shows that the resting state or most abundant surface intermediate (MASI) for the $ReO_4$ species at methanol partial pressure >~120 mbar is Re(—OSi)(—OH)(=O)$_2$(—$OCH_3$), containing dissociatively adsorbed methanol.

The oxidation state of atomically dispersed $ReO_4$ species was probed with in situ XANES measurements for preoxidized 5 wt % ReOx/SBA-15 and under methanol carbonylation reaction conditions where kinetic measurements and in situ FTIR show that $ReO_4$ species should be saturated with —$OCH_3$ (150 mbar methanol, 200 mbar CO and 250° C.). The XANES region did not change due to exposure to reaction conditions demonstrating that Re was in a +7 oxidation state in the most occupied state in the reaction cycle, consistent with the proposal above (data not shown). While the XANES region of 5 wt % ReOx/SBA-15 was indistinguishable comparing preoxidized and under reaction conditions, changes in the EXAFS region were observed (see FIG. 15). The intensity of the scattering feature associated with scattering from oxygen in the first coordination shell of Re decreased under reaction conditions. These changes could be consistent with a decreased coordination number to shorter Re=O bonds and increased coordination to longer Re—O bonds that have weaker scattering intensity (see FIG. 16). It is possible that CO-induced restructuring of ReOx species. The in situ XANES and EXAFS under reaction conditions are consistent with the proposed MASI described above.

As shown in Scheme 1, AA formation on atomically dispersed $ReO_4$ active sites on $SiO_2$ occurs through dissociative methanol adsorption to form Re(—O—Si)(—OH)(=O)$_2$(—$OCH_3$).

Scheme 1. Proposed mechanism for acetic acid formation on atomically dispersed $ReO_4$ species

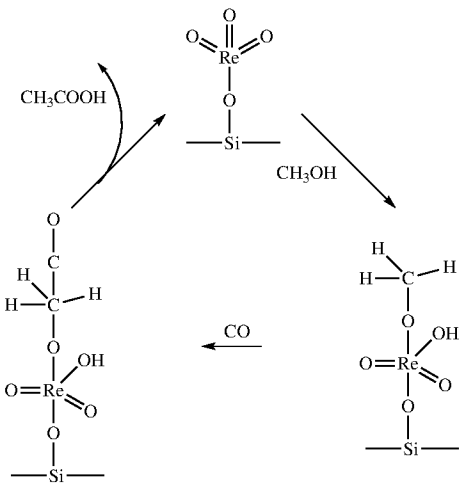

On the basis of the partial pressure dependent methanol reaction order for AA formation, in situ FTIR, and in situ XAS, this species is the MASI when the methanol partial pressure is >120 mbar. Because the AA formation rate is first order in methanol and CO at lower methanol partial pressures, the RDS is CO insertion into the terminal $CH_3$ group of the Re(—O—Si)(—OH)(=O)$_2$(—$OCH_3$) species. Typically, for methanol carbonylation on homogeneous Rh catalysts, CO insertion is a migratory process into the M-C bond of Rh—$CH_3$ species (Sunley, et al., *Catal. Today*, 2000, 58 (4), 293-307; Haynes, et al., *J. Am. Chem. Soc.*, 2004, 126 (9), 2847-2861; Maitlis, et al., *J. Chem. Soc., Dalton Trans.*, 1996, 11, 2187-2196). Given the proposed M-O—$CH_3$ structure for $ReO_4$ active sites, a similar CO insertion into the carbon end of the bound —O—$CH_3$ species followed by the rearrangement to acetyl group occurs for $ReO_4$ active sites. Finally, the proton transfers back to form AA that desorbs, leaving $ReO_4$ intact (see FIG. 15). The rate law for AA formation within this mechanism can be written as:

$$AA \text{ Production Rate} = \frac{k_2 K_1 P_{CO} P_{CH_3OH}}{1 + K_1 P_{CH_3OH}}$$

where $K_1$ is the equilibrium constant for dissociative methanol adsorption and $k_2$ is the rate constant for the gas phase attack of CO on surface bound methoxy. At lower methanol partial pressure, vacant sites are abundant, and the denominator of the rate law is approximately equal to 1; thus, the rate law appears as a first-order with respect to methanol and CO partial pressures. In contrast, at higher methanol partial pressures, active sites are saturated with dissociatively adsorbed methanol and the denominator becomes $K_1 P_{CH_3OH}$, which results in a zero-order dependence of AA formation on the methanol partial pressure.

An order of magnitude increase in DME production rate comparing atomically dispersed $ReO_4$ and ReOx clusters was observed, where contiguous acidic sites likely exist on the cluster surfaces, FIG. 2b. On 10 wt % ReOx/SBA-15, the DME formation rate exhibited a second-order dependence on methanol up to ~100 mbar and a transition to a zero-order at higher partial pressures (see FIG. 17A). Conversely, on ReOx clusters (20 wt % Re), the DME formation rate was inhibited at methanol partial pressures >85 mbar. The second order dependence on methanol partial pressure is consistent with the bimolecular reaction leading to DME formation. The data in FIG. 17A shows that ReOx clusters can support supramonolayer methanol or methoxy coverage, which cannot occur on atomically dispersed $ReO_4$ active sites. Both catalysts exhibited a negative CO reaction order for DME formation, which shows a competition between CO and methanol in reactions with adsorbed —$OCH_3$ species (see FIG. 17B).

Example 6. $ReO_4/SiO_2$ Reactivity is Promoted with Atomically Dispersed Rh

Materials and Methods

For the synthesis of atomically dispersed Rh—$ReO_4$ pair sites on $SiO_2$, appropriate amounts of $HReO_4$ were dissolved in 10 mL of HPLC grade water and the desired amounts of TEA (TEA/Re molar ratio of 8:1) were added into the solution under magnetic stirring for 30 min to ensure the solution was well mixed, following which appropriate amounts of rhodium(III) chloride (Sigma-Aldrich, 307866) were added into the solution, and the mixture was stirred for another 30 min. The precursor solution was injected via syringe pump (5 mL/h) into a 100 mL suspension of the SBA-15 support under magnetic stirring. After being mixed for 12 h at room temperature, the solution was dried at 80° C. using a rotary evaporator. The prepared catalysts were calcined at 450° C. for 4 h under dry air prior to characterization and reactivity measurements.

Results

From the kinetic data, it is shown that features of the $ReO_4/SiO_2$ active site that allow high AA selectivity are (i) reduced rates of DME formation, which may result from the effective blocking of the associative DME formation pathway by the isolated active sites, and (ii) the ability of CO to outcompete methanol in the attack on the terminal $CH_3$ in bound —$OCH_3$ species (Corma, et al., *J. Am. Chem. Soc.*, 2008, 130(48), 16316-16323; Boronat, et al., *Phys. Chem. Chem. Phys.*, 2011, 13(7), 2603-2612). The formation of Rh—ReOx pair-sites on $SiO_2$ should further promote the AA production rate on atomically dispersed $ReO_4$ active sites. Atomically dispersed Rh—ReOx pair-sites catalysts were prepared and characterized by CO probe molecule FTIR (Ro, et al., *ACS Catal.*, 2019, 9, 10899-10912).

FIG. 18A shows CO probe molecule FTIR spectra for 0.2 wt % $Rh/SiO_2$ and 0.2 wt % Rh-10 wt % ReOx/SBA-15 at saturation coverage and room temperature. The Rh-ReOx/SBA-15 catalysts are also referred herein as "Rh/Re—$SiO_2$" catalysts. For example, the 0.2 wt % Rh-10 wt % ReOx/SBA-15 catalyst is also referred herein as a "0.2% Rh/10% Re—$SiO_2$" catalyst. Two strong bands centered at 2091 and 2030 cm$^{-1}$ were observed for 0.2 wt % $Rh/SiO_2$, which are assigned to the symmetric and asymmetric stretches of the $Rh(CO)_2$ gem-dicarbonyl species, demonstrating the predominant existence of atomically dispersed Rh species (Yates, et al., *J. Chem. Phys.*, 1983, 79 (2), 1026-1030; Miessner, et al., *J. Mol. Catal.*, 1986, 36 (1986), 369-373). Another CO stretch at 2107 cm$^{-1}$ was observed, which was assigned to an atomically dispersed Rh species that is simultaneously coordinated to CO and an additional O (Rice, et al., *J. Chem. Phys.*, 1981, 74 (11), 6487-6497). A blue-shift of ~6 cm$^{-1}$ in the CO stretch frequency for $Rh(CO)_2$ species was observed comparing Rh/ReOx-$SiO_2$ and $Rh/SiO_2$. The CO stretch frequency in $Rh(CO)_2$ depends on the supports ability to withdraw or donate charge to Rh. Thus, the blue shift is evidence that Lewis acidic ReOx species reduced the charge transfer to CO species bound to Rh (Lwin, et al., *ACS Catal.*, 2015, 5 (3), 1432-1444; Ro, et al., *ACS Catal.*, 2019, 9, 10899-10912; Hoffman, et al., *ACS Catal.*, 2018, 8 (4), 3489-3498). A similar blue shift in CO frequency was correlated with the formation of Rh—Re atomically dispersed pair sites on $Al_2O_3$ through correlation with HAADF-STEM imaging, providing confidence in the formation of Rh—Re atomically dispersed pair sites in the current catalyst.

Methanol carbonylation reactivity measurements at 30 mbar methanol and CO as a function of temperature are shown in FIG. 18B for 10 wt % ReOx/SBA-15 and 0.2 wt % Rh/10 wt % ReOx/SBA-15. This comparison showed an order of magnitude increase in the rate of AA formation, without promoting DME formation (see FIG. 19) and with the addition of 0.2 wt % Rh. This results in an increase of AA selectivity to ~96%, even at the stoichiometric, low pressure feed conditions used here. It is noted that 0.2 wt % $Rh/SiO_2$ showed no measurable methanol conversion under these conditions. Eapp for AA production was measured to be 155±20 and 133±27 kJ mol$^{-1}$ for 10 wt % ReOx/SBA-15 and 0.2 wt % Rh/10 wt % ReOx/SBA-15, respectively (see FIG. 20). This difference in Eapp is consistent with the difference in Eapp for AA production on the 1, 5, and 10 wt % ReOx/SBA-15 catalysts (see FIG. 2A), showing Rh may be selectively promoting AA formation on $ReO_4$ species rather than modifying the inherent barrier. CO preferentially adsorbs on atomically dispersed Rh compared to methanol or methanol-derived intermediates (Tang, et al., *Nat. Commun.*, 2018, 9 (1), 1-11; Fielicke, et al., *J. Phys. Chem. B*, 2004, 108(38), 14591-14598). Thus, the formation of $Rh(CO)_2$ species promotes the attempt frequency of CO insertion into neighboring Re—$OCH_3$ species.

On the basis of the above-described results, the addition of ~0.2 wt % of atomically dispersed Rh to 10 wt % atomically dispersed $ReO_4$ (i.e. Rh-ReOx) on $SiO_2$ increased AA selectivity to more than 96%, resulting in volumetric AA production rates comparable to homogeneous processes.

Example 7. The Volumetric AA Production Rates on Rh—$ReO_4/SiO_2$ Catalyst are on Par with Those of the Monsanto Process Materials and Methods The volumetric and per metal site reaction rates of AA production on atomically dispersed $ReO_4$/SBA-15 and Rh—$ReO_4$/SBA-15 were calculated and compared with other heterogeneous and homogeneous systems (see Table 4).

TABLE 4

Comparison with other systems for methanol carbonylation to AA.

| | AA production rate | AA production rate (mmol dm$^{-3}$ s$^{-1}$)$^a$ | CO/methanol molar ratio | Reactor pressure | Reaction temperature | Iodide promotor |
|---|---|---|---|---|---|---|
| 10% ReOx/SBA-15 | 0.02 mmol g$_{Re}^{-}$ 1s$^{-1}$ | 0.13 | 1:1 | 1 atm | 280° C. | |
| 0.2% Rh/SiO$_2$ | 0 | 0 | 1:1 | 1 atm | 280° C. | |
| 0.2% Rh-10% ReOx/SBA-15 | 0.2 mmol g$_{Re}^{-}$ 1s$^{-1}$ | 1.3 | 1:1 | 1 atm | 280° C. | |
| 1.3% Cu-MOR | 0.07 mmol g$_{Cu}^{-}$ 1s$^{-1}$ | 0.2 | 200:1 | 50 atm | 270° C. | |
| 1% Ir-0.7% La/AC | 0.15 mmol g$_{Ir}^{-1}$s$^{-1}$ | 1.4 | 1:1 | 25 atm | 230° C. | CH$_3$I |
| 2.5% Ni/AC | 1.47 mmol g$_{Ni}^{-}$ 1s$^{-1}$ | 1.8 | 1:1 | 11 atm | 300° C. | CH$_3$I |
| 0.265% Rh/POL-2BPY | 3.9 mmol g$_{Rh}^{-}$ 1s$^{-1}$ | 0.3 | 1:1 | 35 atm | Below 200° C. | CH$_3$I |
| Monsanto Process (Homogenous) | | 1.5 | 2:1 | 30-60 atm | Below 200° C. | HI |
| Cativa Process (Homogenous) | | 5.5 | | 28 atm | 190° C. | HI |

$^a$Unit conversion from mmol/g/s to mmol/dm$^3$/s was estimated using catalyst densities and volume fractions.

Results

As shown in Table 4, the AA production rates on a per g of metal basis observed for the Re-based catalysts reported here are competitive with Cu modified zeolites (Yashima, et al., *J. Catal.*, 1979, 59(1), 53-60; Ni, et al., *Catal. Sci. Technol.*, 2017, 7(20), 4818-4822), atomically dispersed Rh on polymer supports (Ren, et al., *J. Catal.*, 2019, 369, 249-256), and atomically dispersed Ir—La site pairs (Kwak, et al., *J. Phys. Chem. Lett.*, 2014, 5(3), 566-572; Ren, et al., *Chin. J. Catal.*, 2018, 39 (6), 1060-1069), albeit in the absence of high operating pressure, high CO/MeOH feed ratios, and halide cofeeds. The volumetric AA production rates on the Rh—ReO$_4$/SBA-15 catalyst in a fixed bed process are on par with those of the Monsanto process and a few-fold lower than those of the Cavita process (Maitlis, et al., *J. Chem. Soc., Dalton Trans.*, 1996, 11, 2187-2196). This comparison demonstrates the substantial potential and operational advantages of the Rh—ReO$_4$/SBA-15 catalyst reported here. Given that the reaction rates reported here are from measurements at ~30 mbar CO and methanol, and that first order behavior in CO was observed up to 600 mbar partial pressure, it is expected that operation at higher pressure equimolar CO and methanol feeds will significantly further promote volumetric AA production rates. Further, optimization of the Rh and Re loadings on the basis of volumetric production rate per catalyst cost will allow further optimization of catalyst performance

Example 8. The ReOx/SBA-15 Catalysts Catalyze Methyl Acetate Carbonylation to Acetic Anhydride Materials and Methods Atomically dispersed ReO$_4$/SBA-15 was tested for methyl acetate carbonylation to produce acetic anhydride (CH$_3$CO)$_2$O. The catalytic activity for methanol carbonylation was evaluated in a fixed-bed quartz reactor in the temperature of 240, 260 and 280° C. operating at atmospheric pressure. All gas flows were controlled by mass flow controllers (Teledyne Hastings) and an in-line bubbler was used to deliver gas phase methyl acetate (Sigma-Aldrich, HPLC Grade, CAS 79-20-9) to the catalyst. Helium (Airgas, UHP, 99.999%) was used to bubble methyl acetate.

The reaction effluent was quantified with online mass spectrometry (HALO 201, Hiden Analytical Inc.). The following m/z values were used to detect each product: m/z=28 for CO, m/z=74 for methyl acetate, and m/z=87 for acetic anhydride. The concentrations were calibrated to the signal intensity at each mass and He was used as an internal standard.

Prior to reactivity measurements catalysts were pretreated by oxidation at 350° C. for 1 hour with pure O$_2$ at 50 mL min$^{-1}$, followed by measurements at varying temperatures. The system was allowed two hours at each temperature to ensure steady state was achieved. 200 mg of 10 wt % ReOx/SBA-15 was then exposed to a gas mixture of methyl acetate and CO at a molar ratio of 1:1 for reactivity measurements (177 mbar methyl acetate and 177 mbar CO with balance inert). At the temperature of 240, 260 and 280° C., mass spectrometry analysis was employed to detect methyl acetate and CO for conversion calculation and the desired product acetic anhydride.

Results

This reaction was previously reported to achieve in the homogeneous system containing a nickel, rhodium or iridium source and iodide cocatalyst. The reaction started from iodide salts reaction with methyl acetate to generate methyl iodide and the corresponding acetate salts (Polichnowski, *J. Chem. Educ.*, 1986, 63 (3), 206-209). Oxidative addition of methyl iodide to metal produced methyl-metal species, followed by the rapid insertion of carbon to yield an acyl-metal species (Schrod and Luff, *Ind. Eng. Chem. Prod. Res. Dev.*, 1981, 20 (4), 649-653). Finally, the reductive elimination of acetyl iodide regenerated the active metal sites (Conifer, et al., *Organometallics*, 2011, 30 (15), 4060-4066; Gong, et al., *J. Mol. Catal. A Chem.*, 1999, 147 (1-2), 113-124). The production of acetic anhydride was obtained either by the reaction of acetyl iodide with methyl acetate or by the reaction of acetyl iodide with acetate salts and this step was believed to be the rate limiting step (Polichnowski, *J. Chem. Educ.*, 1986, 63 (3), 206-209; Marr, et al., *Inorg. Chem. Commun.*, 2000, 3 (11), 617-619). The proposed mechanism for methyl acetate carbonylation on atomically dispersed ReO$_4$ species is methyl acetate being activated to methyl and acetyl on ReO$_4$ followed by CO insertion into the methyl group (see Scheme 2). The surface —CH$_3$—CO reacts with —O—(CO)—CH$_3$ species to produce acetic anhydride and regenerate ReO$_4$ species.

Scheme 2. Proposed mechanism for acetic anhydride formation on atomically dispersed ReO$_4$ species

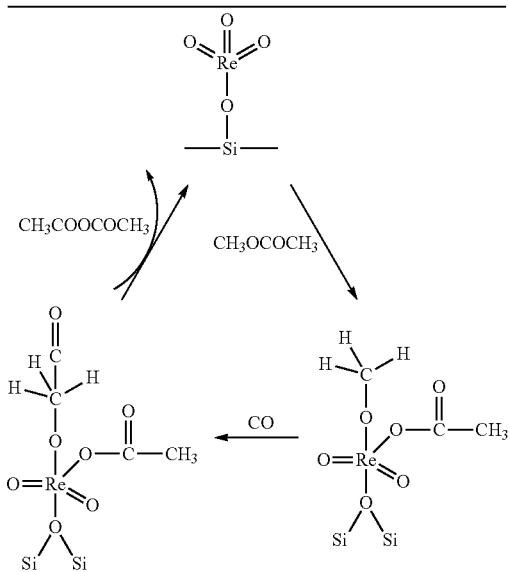

Methyl acetate conversion increased from 0.5% to 9% as temperature increased from 240 to 280° C. (see FIG. 21A). Acetic anhydride production rates in the explored temperature range increased from 0.0004 to 0.0028 mmol s$^{-1}$ g$_{Re}^{-1}$ (see FIG. 21B). As shown in FIG. 21C, the selectivity to acetic anhydride decreased from 22% to 17% in this temperature range.

The data in the Examples shows that ReO$_x$ sites of ReOx/SBA-15 catalysts with ≤10% Re weight loading are atomically dispersed (i.e. isolated ReO$_4$ species on inert SiO$_2$ support). Atomically dispersed ReO$_4$ species on inert SiO$_2$ supports were observed to be heterogeneous carbonylation catalysts (e.g. methanol carbonylation or methyl acetate carbonylation) without the need for a halide cofeed. In methanol carbonylation, the catalytic process exhibited mechanistic similarities to zeolite-based carbonylation catalysts, although the Re-based catalysts promote CO insertion into methoxy species to produce AA, while zeolite catalysts favor methanol insertion into methoxy species prior to carbonylation. The combination of these ReOx/SBA-15 catalysts with Rh or other metals allows further improvements in AA production rates and selectivity. Through promotion of the atomically dispersed ReOx/SBA-15 with atomically dispersed Rh, AA production rates rivaling reports of the Monsanto process were achieved. Other dispersed strong Lewis acids (e.g. AlO$_x$, WO$_x$, MoO$_x$) on inert supports (mesoporous SiO$_2$ or carbon-based materials) may provide similar reactivity. This work introduces a new class of methanol carbonylation catalysts and discusses how atomically dispersed pairs sites could act cooperatively to drive catalytic processes.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for alcohol carbonylation or ester carbonylation comprising (i) exposing a mixture of one or more alcohols or one or more esters and carbon monoxide to a catalyst, wherein the one or more alcohols or one or more esters and carbon monoxide are in the gas phase,
   wherein the catalyst comprises a support; and
   a metal oxide,
       wherein the metal oxide is dispersed on the surface of the support, and
       wherein at least 10% of the metal oxide is atomically dispersed on the surface of the support.

2. The method of claim 1, wherein the one or more alcohols are C1-C20 alcohols, and wherein the one or more esters are methyl acetate, methyl propionate, or methyl butyrate, or a combination thereof.

3. The method of claim 1, wherein the catalyst is stable for at least 40 hours at a temperature between 100° C. and 350° C., and a pressure between 0 bar and 50 bar.

4. The method of claim 1, further comprising oxidizing the metal oxide with an oxidizing gas prior to step (i) and/or recycling a gas stream after step (i).

5. The method of claim 1, wherein the method is for alcohol carbonylation, and wherein step (i) is performed at a temperature between 100° C. and 350° C., and under a pressure of up to 50 bar; or
   wherein the method is for ester carbonylation, and wherein step (i) is performed at a temperature between 100° C. and 350° C., and under a pressure of up to 1 bar.

6. The method of claim 1, wherein the method is for alcohol carbonylation, and wherein the one or more alcohols have a single-pass conversion of at least 10%; or
   wherein the method is for ester carbonylation, and wherein the one or more esters have a single-pass conversion of at least 0.5%.

7. The method of claim 1, wherein the method is for alcohol carbonylation, and wherein the one or more alcohols are converted to corresponding carboxylic acids at a production rate of at least 0.007 mmol s$^{-1}$ g$_{metal}^{-1}$; or
   wherein the method is for ester carbonylation, and wherein the one or more esters are converted to corresponding anhydrides at a production rate of at least 0.0004 mmol s$^{-1}$ g$_{metal}^{-1}$.

8. The method of claim 1, wherein the method is for alcohol carbonylation, and wherein the one or more alcohols are converted to the corresponding carboxylic acids with a selectivity of at least 60%; or
   wherein the method is for ester carbonylation, and wherein the one or more esters are converted to corresponding anhydrides with a selectivity of at least 10%.

9. The method of claim 1, wherein the support of the catalyst comprises a chemically inert material.

10. The method of claim 1, wherein the support of the catalyst comprises a mesoporous material or a microporous material.

11. The method of claim 1, wherein the support of the catalyst comprises mesoporous material and the mesoporous material has an average pore diameter from 1 nm to 50 nm.

12. The method of claim 1, wherein the support of the catalyst has a surface area of at least 50 m²/g.

13. The method of claim 1, wherein the support of the catalyst comprises silicon dioxide or a carbon-based material.

14. The method of claim 1, wherein the support of the catalyst is in the form of a sheet or nanoparticle.

15. The method of claim 1, wherein the support is silicon dioxide.

16. The method of claim 1, wherein the metal oxide comprises rhenium.

17. The method of claim 1, wherein the metal oxide comprises a first metal selected from the group consisting of rhenium, aluminum, tungsten, and molybdenum.

18. The method of claim 17, wherein the first metal is present in an amount in the range between 0.1 wt % and 10 wt % of the catalyst.

19. The method of claim 17, wherein the metal oxide further comprises a second metal selected from the group consisting of rhodium, iridium, and palladium.

20. The method of claim 19, wherein the second metal is present in an amount in the range between 0.05 wt % and 5 wt % of the catalyst.

* * * * *